US012242662B2

(12) United States Patent
Verner et al.

(10) Patent No.: US 12,242,662 B2
(45) Date of Patent: Mar. 4, 2025

(54) HAND PRESENCE SENSING AT CONTROL INPUT DEVICE

(71) Applicant: Intuitive Surgical Operations, Inc., Sunnyvale, CA (US)

(72) Inventors: Lawton N. Verner, San Jose, CA (US); Jason W. Hemphill, Los Gatos, CA (US); Brian Luptak, Santa Clara, CA (US); Ashwinram Suresh, San Jose, CA (US); Clifford N. Bargar, San Francisco, CA (US); Hsien-Hsin Liao, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 282 days.

(21) Appl. No.: 17/766,592

(22) PCT Filed: Oct. 7, 2020

(86) PCT No.: PCT/US2020/054558
§ 371 (c)(1),
(2) Date: Apr. 5, 2022

(87) PCT Pub. No.: WO2021/071933
PCT Pub. Date: Apr. 15, 2021

(65) Prior Publication Data
US 2022/0382364 A1 Dec. 1, 2022

Related U.S. Application Data

(60) Provisional application No. 62/912,536, filed on Oct. 8, 2019.

(51) Int. Cl.
*G06F 3/01* (2006.01)
*A61B 34/00* (2016.01)
(Continued)

(52) U.S. Cl.
CPC .............. *G06F 3/011* (2013.01); *A61B 34/37* (2016.02); *A61B 34/74* (2016.02); *G06F 3/0338* (2013.01); *G06F 3/038* (2013.01); *G06F 3/0304* (2013.01)

(58) Field of Classification Search
None
See application file for complete search history.

(56) References Cited

U.S. PATENT DOCUMENTS 5,367,257 A * 11/1994 Garshelis ................ G01P 13/04
324/207.2
5,876,325 A 3/1999 Mizuno et al.
(Continued)

FOREIGN PATENT DOCUMENTS

EP 3040802 A2 * 7/2016 .............. F24F 11/00
EP 3245975 A1 11/2017
(Continued)

OTHER PUBLICATIONS

International Search Report and Written Opinion for Application No. PCT/US2020/054558, mailed Jan. 11, 2021, 18 pages.
(Continued)

*Primary Examiner* — Jaime Figueroa
*Assistant Examiner* — Atticus A Cameron
(74) *Attorney, Agent, or Firm* — IP Spring

(57) ABSTRACT

Implementations relate to hand presence sensing at a control input device. In some implementations, a control input device includes a base member, a handle coupled to the base member and configured to be manually contacted at a grip portion of the handle and moved by a hand of a user in one or more degrees of freedom, one or more control input sensors configured to detect positions or orientations of the handle in the one or more degrees of freedom, and a presence sensor coupled to the base member. The presence (Continued)

sensor has a sensing field, and at least a portion of the sensing field is located proximate to the handle.

20 Claims, 10 Drawing Sheets

(51) Int. Cl.
*A61B 34/37* (2016.01)
*G06F 3/03* (2006.01)
*G06F 3/0338* (2013.01)
*G06F 3/0346* (2013.01)
*G06F 3/0362* (2013.01)
*G06F 3/038* (2013.01)

(56) References Cited

U.S. PATENT DOCUMENTS

| | | | |
|---|---|---|---|
| 6,587,750 | B2 | 7/2003 | Gerbi et al. |
| 8,638,057 | B2 | 1/2014 | Goldberg et al. |
| 8,935,003 | B2 | 1/2015 | Itkowitz et al. |
| 9,283,048 | B2 | 3/2016 | Kostrzewski et al. |
| 9,314,307 | B2 | 4/2016 | Richmond et al. |
| 11,712,314 | B2 * | 8/2023 | Thompson .............. A61B 34/74 606/1 |
| 2010/0069940 | A1 | 3/2010 | Miller et al. |
| 2010/0303301 | A1 * | 12/2010 | Lamoureux ............. G06T 7/254 382/107 |
| 2011/0118753 | A1 | 5/2011 | Itkowitz et al. |
| 2014/0018960 | A1 | 1/2014 | Itkowitz |
| 2014/0165770 | A1 | 6/2014 | Abri et al. |
| 2015/0290814 | A1 | 10/2015 | Schiele et al. |
| 2016/0216167 | A1 | 7/2016 | Blumenkranz et al. |
| 2017/0095298 | A1 | 4/2017 | Vakharia et al. |
| 2017/0262045 | A1 * | 9/2017 | Rouvinez ................ G06F 3/011 |
| 2018/0147019 | A1 * | 5/2018 | Farritor ............. G05G 9/04737 |
| 2018/0296294 | A1 | 10/2018 | Ueda |
| 2018/0297211 | A1 | 10/2018 | Schaible et al. |
| 2018/0310997 | A1 | 11/2018 | Peine et al. |
| 2019/0380791 | A1 | 12/2019 | Fuerst et al. |
| 2019/0380801 | A1 | 12/2019 | Savall et al. |
| 2019/0380802 | A1 | 12/2019 | Savall et al. |
| 2019/0380809 | A1 | 12/2019 | Fuerst et al. |
| 2019/0391664 | A1 * | 12/2019 | Josephson ............... G06T 11/60 |

FOREIGN PATENT DOCUMENTS

| | | |
|---|---|---|
| JP | 2006321027 A | 11/2006 |
| WO | WO-2012127404 A2 | 9/2012 |
| WO | WO-2016201544 A1 | 12/2016 |
| WO | WO-2017031132 A1 | 2/2017 |
| WO | WO-2018056894 A1 * 3/2018 ............ G01J 5/0025 |
| WO | WO-2018112227 A2 | 6/2018 |
| WO | WO-2019099504 A1 | 5/2019 |
| WO | WO-2019099584 A1 | 5/2019 |
| WO | WO-2019217882 A1 | 11/2019 |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Office Action for European Application No. 20797927.9, mailed Jun. 5, 2024, 09 pages.

* cited by examiner

HAND PRESENCE SENSING AT CONTROL INPUT DEVICE

CROSS-REFERENCE TO RELATED APPLICATIONS

The present application is a U.S. National Phase application of International Patent Application No. PCT/US2020/054558, filed Oct. 7, 2020 and titled HAND PRESENCE SENSING AT CONTROL INPUT DEVICE, which claims priority to U.S. Provisional Patent Application No. 62/912,536, filed Oct. 8, 2019 and titled HAND PRESENCE SENSING AT CONTROL INPUT DEVICE, the entire contents of both of which are hereby incorporated by reference.

BACKGROUND

Control input devices allow a user to control functions of various types of mechanisms and instruments. Teleoperated surgical devices, for example, can use various types of medical instruments to perform minimally invasive surgical procedures that reduce damage to healthy tissue of patients. The medical instruments can be connected to manipulator devices such as manipulator arms that can be controlled to perform the surgical procedures. Control of the medical instruments at a manipulator device can be provided to an operator at one or more control input devices, which may be at a operator terminal or station. Actuators of the manipulator device can be controlled by a control input device to cause motion or initiate another function of a medical instrument, camera, or other end effector at the manipulator device that interacts with the patient surgical site. In some examples, the control input device at the operator station can be physically manipulated by the operator in one or more degrees of freedom to control the end effector to be moved in coordination with the manipulation of the control device, e.g., to move in corresponding degrees of freedom at the operating site.

In many circumstances, it is desirable for the control system to have the ability to detect the presence of a user operating the control input devices. For example, this allows user control of a manipulator device to be enabled when the user is detected to be operating the control input device, and safely disabled when the user is not detected to be present. In some control systems, the user's presence can be detected using one or more presence sensors. For example, some systems include an operator terminal at which control input devices are used and which includes a video output device. An optical detector can detect the presence of an operator's head when the head is positioned to view the video output device. However, such detection does not directly indicate whether the user's hands are ready to use the control input devices. Furthermore, some control input devices have a structure and/or grips for the user's hands that may cause difficulty in directly sensing presence of user's hands operating the control input device. For example, rotating pincher grips on a control input device can provide a pinching motion, and they may rotate about one or more axes of the control device, which may cause an operator's hand to adopt a variety of configurations. In some cases, the presence of an operating hand in one or more such configurations may not be easily detected by sensors.

SUMMARY

Implementations of the present application relate to hand presence sensing at a control input device. In some implementations, a control input device includes a base member, a handle coupled to the base member and configured to be manually contacted at a grip portion of the handle and moved by a hand of a user in one or more degrees of freedom, one or more control input sensors configured to detect positions and/or orientations of the handle in the one or more degrees of freedom, and a presence sensor coupled to the base member. The presence sensor has a sensing field, and at least a portion of the sensing field is located proximate to the handle.

Various implementations and examples of the control input device are described. For example, in some implementations, the presence sensor is configured to detect electromagnetic radiation or an ultrasonic wave that is directed through space to the presence sensor by a presence of the hand in the sensing field of the presence sensor. In some implementations, the presence sensor is located on a surface of the handle that is not contacted by the hand during operation of the control input device. In some implementations, the portion of the sensing field is located in an approach path of the hand when moving toward the handle prior to operating the handle. In some implementations, the handle is external to the sensing field.

In some implementations, the sensing field is shaped as, or approximately as, a cone that increases in width in a direction away from the presence sensor. In some implementations, the sensing field has a spatial position fixed with respect to a central axis of the handle that extends between a distal end and a proximal end of the handle. In some implementations, the handle at least partially extends into the sensing field. In some implementations, the sensing field is located at least partially in front of an end of the handle.

In some implementations, the presence sensor is a first presence sensor, the sensing field is a first sensing field located at a first side of the handle, and the control input device further includes a second presence sensor coupled to the base member and configured to detect second electromagnetic radiation that is directed through space to the second presence sensor by a presence of the hand in a second sensing field of the second presence sensor. The second sensing field is proximate to the handle and is located at a second side of the handle that is opposite the first side. For example, the first side can be a first side of a vertical plane intersecting a central axis of the handle and the second side a second side of the vertical plane.

In some implementations, a signal generated by the presence sensor comprises a parameter, and the parameter comprises a value that corresponds to a variable distance between an object in the sensing field and the presence sensor. In some implementations, the presence sensor includes an electromagnetic sensor, which includes an emitter and a detector, the emitter configured to emit a first electromagnetic signal in the sensing field and the detector configured to detect the first electromagnetic signal reflected from the hand in the sensing field. In some implementations, the presence sensor includes an optical time-of-flight sensor that generates a signal comprising a value that corresponds to a variable distance between the hand in the sensing field and the presence sensor. In some implementations, the presence sensor includes a thermopile sensor or thermal imaging camera, that includes a detector configured to detect infrared radiation emitted by the hand in the sensing field. Other types of sensors can also be used, e.g., ultrasonic sensor, etc.

In some implementations, a portion of the handle includes a handle distal end, a handle proximal end opposite the handle distal end, and a central axis defined between the handle distal end and the handle proximal end. The handle distal end is closer than the handle proximal end to the hand. A base portion of the base member includes a base distal end and a base proximal end opposite the base distal end, the base portion extending parallel or approximately parallel to the central axis of the portion of the handle. The presence sensor is located on the base distal end that is closer than the base proximal end to the handle distal end.

In some implementations, the handle includes a central portion that extends along a central axis of the handle between a distal end and a proximal end of the handle, and the handle includes two grip members extending from the central portion. The two grip members are each configured to be gripped by a corresponding finger of the hand, and the central portion is configured to be positioned between at least two fingers of the hand during grip of the handle. The sensing field is configured to cover a region including one or more fingers of the hand touching either of the two grip members. In some implementations, the one or more degrees of freedom include a roll degree of freedom, in which the handle is rotatable about the central axis of the handle with respect to the base member in the roll degree of freedom, and the sensing field is configured to include at least a portion of the hand at all orientations of the handle in the roll degree of freedom while the hand grips the handle. In various implementations, the base member is optionally mechanically grounded or mechanically ungrounded.

In some implementations, a control input device includes a handle configured to be manually contacted at a grip portion of the handle and moved by a hand of a user in one or more degrees of freedom. The handle includes a central portion that extends along a central axis of the handle, and the central portion is configured to be positioned between at least two fingers of the hand during a grip of the handle by the hand. One or more control input sensors are configured to detect positions or orientations of the handle in the one or more degrees of freedom, and a presence sensor is coupled to a distal end of the handle that is proximate to the hand. The presence sensor is configured to detect electromagnetic radiation or an ultrasonic wave that is directed through space to the presence sensor by a presence of the hand in a sensing field of the presence sensor, and the sensing field is located proximate to the handle.

Various implementations and examples of this control input device are described. For example, in some implementations, the handle is configured such that a palm of the hand is out of contact with the handle while the hand grips the grip portion of the handle. In some implementations, the presence sensor is configured to detect the electromagnetic radiation or the ultrasonic wave by a presence of the palm of the hand in the sensing field of the presence sensor. In some implementations, a signal generated by the presence sensor comprises a parameter, and the parameter comprises a value that corresponds to a variable distance between the detected hand and the presence sensor. In further examples, the parameter includes a value that corresponds to a direction of motion of the hand in the sensing field relative to the presence sensor or a velocity of the hand in the sensing field. In some examples, the value is provided to a processor and is usable to determine whether the hand is operating the control input device. In various implementations, the sensing field is located in an approach path of the hand when moving toward the handle prior to operating the handle, the handle is positioned external to the sensing field, and/or the sensing field is positioned at least partially in front of an end of the handle. In some implementations, the sensing field is shaped as, or approximately as, a cone that increases in width in a direction away from the presence sensor, and the sensing field has a spatial position fixed with respect to a central axis of the handle extending between a distal end and a proximal end of the handle. The presence sensor can include: an electromagnetic sensor that includes an emitter configured to emit a first electromagnetic signal in the sensing field and a detector configured to detect the first electromagnetic signal reflected from the hand in the sensing field; a thermopile sensor that includes a detector configured to detect infrared radiation emitted by the hand in the sensing field; and/or a thermal imaging camera that includes a detector configured to detect the infrared radiation emitted by the hand in the sensing field.

In some implementations, a method includes activating a non-controlling mode in which a handle of a control input device is manually moveable by a user in one or more degrees of freedom without moveably controlling a manipulator device that, e.g., corresponds to the control input device, the manipulator device being in communication with the control input device. In the non-controlling mode, a presence of a hand of a user relative to the handle is sensed in a sensing field of a presence sensor. A portion of the sensing field is located proximate to the handle. In response to sensing the presence of the hand, a controlling mode of the control input device is activated in which the handle is moveable by the user in the one or more degrees of freedom to moveably control the manipulator device. In some implementations of the method, the presence sensor is configured to detect electromagnetic radiation or an ultrasonic wave that is directed through space to the presence sensor by a presence of the hand in a sensing field of the presence sensor. In some implementations, sensing the presence of the hand includes sensing an approach of the hand toward the handle while the hand is in the sensing field prior to contacting and operating the handle.

In some implementations of the method, sensing the approach of the hand toward the handle includes determining a direction of motion of the hand relative to the handle and determining whether the direction of motion is toward the handle. In some implementations, the method further includes determining a velocity of the hand relative to the handle and determining that the velocity of the hand meets (e.g., is less than) a threshold velocity, and the activation of the controlling mode is performed in response to the velocity of the hand meeting the threshold velocity. In some implementations, the method further includes activating the non-controlling mode in response to sensing an indication that the hand is no longer operating the handle. In various implementations, the indication includes sensing the hand outside a threshold distance from the handle, and/or sensing the hand moving in a particular direction relative to (e.g., away from) the handle. In some implementations of the method, activating the controlling mode is performed only in response to both sensing the presence of the hand and sensing a presence of the user by one or more other presence detection devices of a system that includes the control input device, and the one or more other presence detection devices include a grip sensor of the control input device and/or a head presence sensor of the system.

In some implementations, the method further includes, while in the controlling mode, determining a position of the hand relative to a reference location of the control input device, and determining, based on the position of the hand, one or more characteristics of force to be output on the control input device, the one or more characteristics of force including a maximum force magnitude output on the control input device, a gain of force magnitude output on the control input device, and/or a rate at which the force magnitude on the control input device is increased. In some implementations, the method further comprises, while in the controlling mode, determining a position of the hand relative to a reference location of the control input device, and adjusting a safety feature of the control input device based on the position, including: changing parameters used in detection of patterns of motion, acceleration, or direction of the control input device to detect active use of the control input device by the user, and/or physically limiting a velocity of the control input device in one or more degrees of freedom by using one or more force output devices coupled to a mechanism of the control input device.

In some implementations, the method further includes, in the controlling mode, determining a position of the hand relative to a reference location of the control input device, and determining detection parameters of one or more other presence sensors of the control input device based on the position; the other presence sensors are independent and separate from a hand presence sensing system that performs the sensing of the presence of the hand, and the detection parameters include a threshold of sensing, a range of sensing, and/or a duration of sensing. In some implementations, the method further includes, in the controlling mode, detecting presence of the user by one or more other presence sensors of the control input device, and determining one or more detection parameters of a hand presence sensing system based on the detected presence of the user by the one or more other presence sensors, the other presence sensors being independent and separate from the hand presence sensing system that performs the sensing of the presence of the hand, and the one or more detection parameters of the hand presence sensing system including a threshold of sensing, a range of sensing, and/or a duration of sensing.

In some implementations, a method includes activating a controlling mode in which a handle of a control input device is manually moveable by a user in one or more degrees of freedom to moveably control a manipulator device that is in communication with the control input device. The method includes, in the controlling mode, sensing a presence of a hand of the user relative to the handle in a sensing field of a presence sensor, a portion of the sensing field positioned proximate to the handle, and in response to sensing the presence of the hand, activating a non-controlling mode in which the handle is moveable by the user in the one or more degrees of freedom without moveably controlling the manipulator device. In some implementations, sensing the change in presence of the hand includes sensing the hand outside a threshold distance from the handle, and/or sensing the hand moving in a direction away from the handle. In some implementations, the method further includes, prior to activating the controlling mode, sensing the presence of the hand in the sensing field of the presence sensor and sensing a presence of the user by one or more other presence detection devices of a system that includes the control input device, the other presence detection devices including a grip of the control input device and/or a head presence sensor of the system, and activating the controlling mode is performed only in response to sensing the presence of the hand and sensing the presence of the user by the one or more other presence detection devices.

In some implementations, a control input device includes handle means for being manually contacted at a grip portion of the handle means and for being moved by a hand of a user in one or more degrees of freedom, means for sensing positions or orientations of the handle means in the one or more degrees of freedom, and means for detecting a hand in a sensing field proximate to and external to the handle means. In some implementations, the means for detecting includes means for detecting electromagnetic radiation or an ultrasonic wave that is directed through space to the means for detecting by a presence of the hand in a sensing field of the means for detecting. In some implementations, the control input device further comprises base means for coupling the handle means to a mechanical ground. In some implementations, the means for detecting is located at a distal end of the handle means that is proximate to the hand. In some implementations, the means for detecting is located at a distal end of a base portion of the base means, and the base portion extends approximately parallel to a central axis of the handle means.

DETAILED DESCRIPTION

Figure 1:
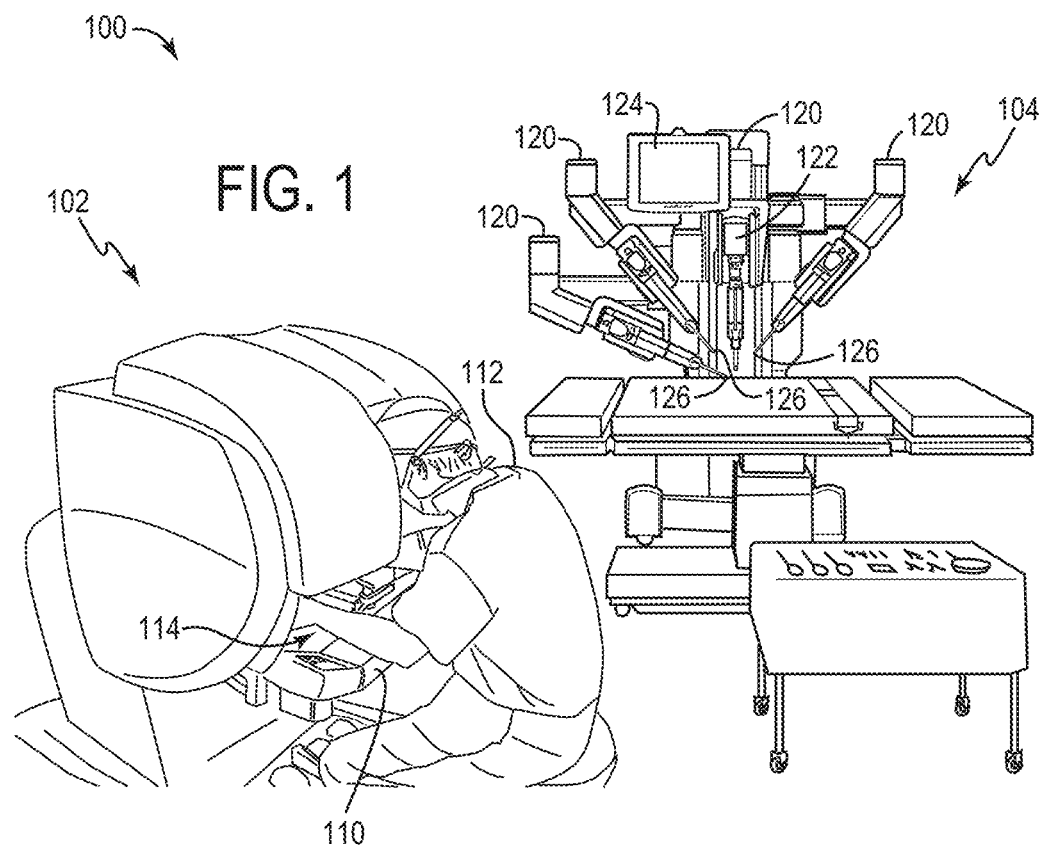
FIG. 1 is a diagrammatic illustration of an example implementation of a teleoperated system which can be used with one or more features disclosed herein, according to some implementations.

One or more implementations described herein relate to control input devices having a hand presence sensing system. The hand presence sensing system is configured to sense the presence of a hand operating a control input device and/or a hand positioned near a control input device. In some implementations, the control input device includes a handle configured to be manually contacted at a grip portion of the handle and moved by a user's hand in one or more degrees of freedom. A presence sensing system includes one or more presence sensors coupled to the handle and/or to a base member that is coupled to the handle. Each presence sensor has a sensing field, and a portion of the sensing field is located proximate to the handle. In some examples, detection of the user's hand in the sensing field, and/or detection of the hand operating the handle, causes the system to enter a controlling mode in which the control input device can control functions of a manipulator device.

In various implementations, the presence sensor is configured to detect electromagnetic radiation or an ultrasonic wave that is directed through space to the presence sensor by a presence of the hand in a sensing field of the sensor. In some examples, the portion of the sensing field can be located in an approach region of the handle, e.g., a region moved into by a hand that is moving toward the handle prior to operating it. The handle can be external to the sensing field, and/or the handle can extend into the sensing field. The sensing field can be positioned at least partially in front of an end of the handle. Multiple presence sensors can each provide a sensing field, e.g., on different sides of a central axis of the handle. The presence sensor can be any of various types, including an electromagnetic sensor (e.g., a time-of-flight sensor), a thermal sensor (e.g., a thermopile sensor or thermal imaging camera operative to detect infrared radiation emitted by the hand in the sensing field), an ultrasonic sensor, etc.

Features described herein provide a control input device with several advantages. In some prior systems, the lack of a positive indication that a user's hand is controlling a user input device may result in a situation in which a manipulator device moves as a result of a corresponding control input device movement, but the control input device movement was unplanned. For example, to avoid unintended manipulation of a manipulator device even if a user is viewing a display screen on which an image of the manipulator device is shown, control over the manipulator device by a control input device can be enabled only if the user's hand is positioned to control the control input device properly. Also, if motors on the control input device are used to provide haptic feedback for a user, a situation may exist in which the haptic feedback could push the control input device away from the user's hand if the user's hand does not have a proper grip on the control input device. Features described herein provide robust detection of a user's hand on or near the control input device, thus allowing a controlled manipulator system to enter a controlling mode even more safely than in systems providing no such hand presence detection.

Furthermore, in some implementations, the described control input device can provide detection of the user's hand within a proximity of the control input device and without contact of any portion of the hand to the surface of the control device by using non-contact sensors. Such non-contact sensors can more reliably sense hand presence than many types of contact sensors. For example, such proximity detection allows more robust hand detection for some types of control input devices that are not operated using direct contact with the palm of a hand, but rather with a user's fingertips or other hand portion (e.g., if the hand encloses a spatial region around the control input device). Described features allow the presence of the hand to be reliably detected when operating such a control input device. Features also allow a system to use the described presence sensing system in conjunction with other presence sensing systems (e.g., sensing of a user's head or other user body portions) to provide more robust user presence detection. This use of multiple sensing features can allow easier and faster detection of user presence in a position to properly operate an input device.

Furthermore, proximity detection allows the system to more robustly determine to enter or exit a controlling mode. For example, detection of the user's hand in the proximity of the control input device alerts the system of the user's intent to grip the control input device handle. In some implementations, the direction of hand movement can be detected, and this detected direction of hand movement allows further detection and determination of user intent. If the user's hand is not in a defined proximity of the control input device, or when the hand is detected to move in a direction relative to the control input device (e.g., in a direction away from the control input device), the detection of hand proximity or direction of hand movement can be used to either exit the controlling mode or to not enter the controlling mode, as the case may be.

Thus, features of the presence sensing system can determine if hand movement near the control input device may be accidental or unintentional based on hand motion. For example, accidental motion of the control input device (e.g., because the control input device was bumped by an object other than the user's hand) can be detected and ignored if the user's hand is not detected near to the control input device. Furthermore, system software can use hand detection information to make decisions about system operating state and to inform safety algorithms that can trigger actions (e.g., system operating state changes) when necessary. Detected user intent based on hand motion can be used to provide features for displayed user interfaces, other functions of the system, safety features, power-saving features, etc. For example, a user interface (and/or other system components) can be turned on from an unpowered or low-power state if user intent to use the control input device is detected.

Various implementations described herein are compact, robust, and inexpensive. Using various described features, determination by a system to enter and exit controlling mode is made more easily, reliably, and robustly.

The terms "center," "parallel," "perpendicular," "aligned," or particular measurements in degrees, Hertz, or other units as used herein need not be exact and can include typical engineering tolerances. Some implementations herein may relate to various objects in terms of their state in three-dimensional space. As used herein, the term "position" refers to the location of an object or a portion of an object in a three dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw around the Cartesian X, Y, and Z axes). As used herein, the term "pose" refers to the position of an object or a portion of an object in at least one degree of translational freedom and to the orientation of that object or portion of the object in at least one degree of rotational freedom (up to six total degrees of freedom).

As referred to herein, a mechanically grounded unit or device is constrained with respect to possible position and orientation motion in a large working environment (e.g., an operating area or room). Also, such a unit is kinematically coupled to the ground (e.g., mechanically supported by a console, supports, or other object attached to the ground). As used herein, the term "proximal" refers to an element that is close to (or closer to) a mechanical ground and the term "distal" refers to an element that is away from (or further from) a mechanical ground.

The term "finger," as used herein, refers to any digit of the hand, e.g., thumb, index finger, middle finger, ring finger, or pinky finger.

FIG. 1 is a diagrammatic illustration of an example teleoperated surgical system 100 which can be used with one or more features disclosed herein. Other types of control systems or other systems can be used in other implementations involving described features. Teleoperated surgical system 100 includes a user control system (e.g., surgeon's console) 102 and a manipulator system 104.

In this example, the user control system (e.g., surgeon's console) 102 includes a viewer 213 (shown in FIG. 2) where an image of a worksite is displayed during an operating procedure using the system 100. For example, the image can be displayed by a display device, such as one or more display screens, to depict a surgical site during a surgical procedure. A support 110 is provided on which a user 112, e.g., an operator such as a surgeon, can rest forearms while gripping two control input devices 210 and 212 (shown in FIG. 2), one in each hand. The control input devices can be positioned in a workspace 114 disposed inwardly beyond the support 110. When using the user control system 102, the user 112 can sit in a chair in front of the control system 102, position the user's head/eyes in front of the viewer, and grip the control input devices 210 and 212, one in each hand, while resting forearms on the support 110. Additional example details are described below with reference to FIG. 2.

The teleoperated system 100 may also include a manipulator system 104 which can be controlled by the user control system 102. For example, manipulator system 104 can be or include a manipulator device. In some implementations as shown, during a surgical procedure, the manipulator system 104 can be positioned close to a patient on an operating table worksite for surgery (or close to other to other type of worksite), where it can remain stationary until a particular surgical procedure or stage of a procedure is completed.

Manipulator system 104 can include one or more manipulator arm assemblies 120. In some examples, an arm assembly 120 can include multiple links rotatably coupled to each other. Portions of the arm assembly can be actuated with a motor and sensed about rotational axes. In some examples, one or more of the arm assemblies 120 can be configured to hold an image capturing device, e.g., an endoscope 122, which can provide captured images of a portion of the surgical site. In some implementations, the captured images can be transmitted to the viewer of the user control system 102 and/or transmitted to one or more other displays, e.g., a display 124 coupled to the manipulator system 104.

In some examples, one or more of the arm assemblies 120 may each include a surgical instrument 126. Each surgical instrument 126 can include a surgical end effector, e.g., for treating tissue of the patient. An end effector can be provided the degrees of freedom provided by, e.g., the rotation of link members of the associated arm assembly, linear motion by an end effector mechanism, etc. Components in the arm assembly can function as force transmission mechanisms to receive teleoperated servo actuation forces and redirect the received forces to operate components of the end effector. An end effector can include one or more motors or other actuators that operate associated features of the end effector, such as the pitch, yaw, and/or roll of the end effector, opening jaws or moving a blade of the end effector, the output of material transported through a connecting tube (e.g., liquid or other fluids), suction forces, and/or any of a multiple of other end effector functions. End effector mechanisms can include flexible elements, articulated "snake" arms, steerable guide tubes, catheters, scalpel or cutting blade, electro-surgical elements (e.g., monopolar or bipolar electrical instruments), harmonic cutter, scissors, forceps, retractors, dilators, clamps, cauterizing tools, needles, needle drivers, staplers, drills, probes, scopes, light sources, guides, measurement devices, vessel sealers, laparoscopic tools, or other tip, mechanism or device. One example of a surgical manipulator arm is a da Vinci® surgical system instrument manipulator arm in surgical systems commercialized by Intuitive Surgical, Inc. of Sunnyvale, Calif.

In this example, the arm assemblies 120 can be caused to move and articulate the surgical instruments 126 in response to manipulation of corresponding control input devices, e.g., manipulation of the control input devices 210 and 212 (shown in FIG. 2) at the user control system 102 by the user 112. This arrangement allows user 112 to direct surgical procedures at internal surgical sites through minimally invasive surgical apertures. For example, one or more actuators coupled to the arm assemblies 120 can output force to cause links or other portions of the arm assemblies to move in particular degrees of freedom in response to control signals received from the user control system 102. For example, movement of an arm and end effector in one or more degrees of freedom can correspond to movement in one or more degrees of freedom of an associated control input device handle by a user. The user control system 102 can be used within a room (e.g., an operating room) with the manipulator system 104 or can be positioned more remotely from the manipulator system 102, e.g., at a different location than the manipulator system.

Some implementations of the teleoperated system 100 can provide different modes of operation. In some examples, in a non-controlling mode (e.g., safe mode) of the teleoperated system 100, the controlled motion of the manipulator system 104 is disconnected from the control input devices of the user control system 102 in disconnected configuration, such that movement and other manipulation of the control input devices does not cause motion of the manipulator system 104. In a controlling mode of the teleoperated system (e.g., following mode, in which one or more manipulator instruments or other devices follow a corresponding control input device), motion of the manipulator system 104 can be controlled by the control input devices 210 and 212 of the user control system 102 such that movement and other manipulation of the control input devices causes motion of the manipulator system 104, e.g., during a surgical procedure.

Some implementations can be or include a teleoperated medical system such as a da Vinci® Surgical System (e.g., a Model IS3000 or IS4000, marketed as the da Vinci Si® or da Vinci Xi® Surgical System), commercialized by Intuitive Surgical, Inc. of Sunnyvale, Calif. However, features disclosed herein may be implemented in various ways, including in implementations at least partially computer-controlled, controlled via electronic control signals, manually controlled via direct physical manipulation, etc. Implementations on da Vinci® Surgical Systems are merely exemplary and are not to be considered as limiting the scope of the features disclosed herein. For example, different types of teleoperated systems having manipulator devices at worksites can make use of actuated controlled features described herein. Other, non-teleoperated systems can also use one or more described features, e.g., various types of control systems and devices, peripherals, etc.

In some implementations, a controlled manipulator device can be a virtual representation of device, e.g., presented in a graphical simulation provided by a computing device coupled to the teleoperated system 100. For example, a user can manipulate the control input devices 210 and 212 of the user control system 102 to control a displayed representation of an end effector in virtual space of the simulation, similarly as if the end effector were a physical object coupled to a physical manipulator device.

Figure 2:
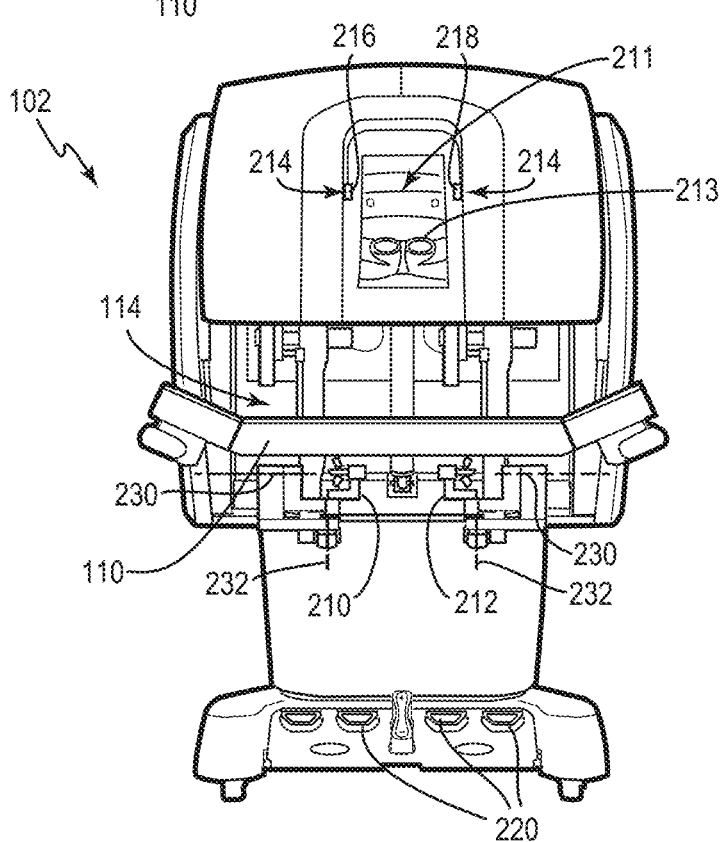
FIG. 2 is a front elevational view of an example user control system as shown in FIG. 1, according to some implementations.

FIG. 2 is a front elevational view of an example user control system 102 as described above for FIG. 1. User control system 102 includes a viewer 213, where an image of a worksite can be displayed during a procedure using the teleoperated system 100. For example, images depicting a surgical site can be displayed during a surgical procedure. The viewer 213 can be positioned within a viewing recess 211 in which the user can position his or her head to view images displayed by the viewer 213. When using the user control system 102, the user 112 can sit in a chair in front of the user control system and position his or her head within the recess 211 such that his or her eyes are positioned in front of the viewer 213.

In some implementations, one or more user presence sensors 214 can be positioned at one or more locations of the user control system 102 to detect the presence of a user located next to or near to the user control system 102. In this example, the user presence sensors 214 can sense a presence of a user's head within the recess 211. For example, an electromagnetic sensor (e.g., optical sensor) can be used for a presence sensor. In some examples, the optical sensor can include an emitter 216 and a detector 218. A beam of infrared or other wavelength of light is emitted from one side of the recess 211 by the emitter 216, and the beam is detected on the other side of the recess by the detector 218. If the beam is interrupted from detection by the detector, e.g., due to the user's head blocking the beam, then the system determines that a user's head is within the recess and that the user is in a proper position to use the control input devices of the user control system 102. Additional or alternative types of presence sensors can be used in various implementations.

Two control input devices 210 and 212 are provided for user manipulation. In some implementations, each control input device 210 and 212 can be configured to control motion and functions an associated arm assembly 120 of the manipulator system 104. For example, a control input device 210 or 212 can be moved in a plurality of degrees of freedom to move a corresponding end effector of the manipulator system 104 in corresponding degrees of freedom. In some implementations, the control input devices are manual input devices which can be moved in all six Cartesian degrees of freedom.

The control input devices 210 and 212 are positioned in workspace 114 inwardly beyond the support 110. For example, a user 112 can rest forearms while gripping the two control input devices 210, 212, with one control input device in each hand. The user also positions his or her head within the viewing recess 211 to view the viewer 213 as described above while manipulating the control input devices 210 and 212. Various examples of portions of input devices that can be used as control input devices 210 and 212 are described below.

Some implementations of user control system 102 can include one or more foot controls 220 positioned below the control input devices 210 and 212. The foot controls 220 can be depressed, slid, and/or otherwise manipulated by a user's feet to input various commands to the teleoperated system while the user is sitting at the user control system 102.

Figure 3:
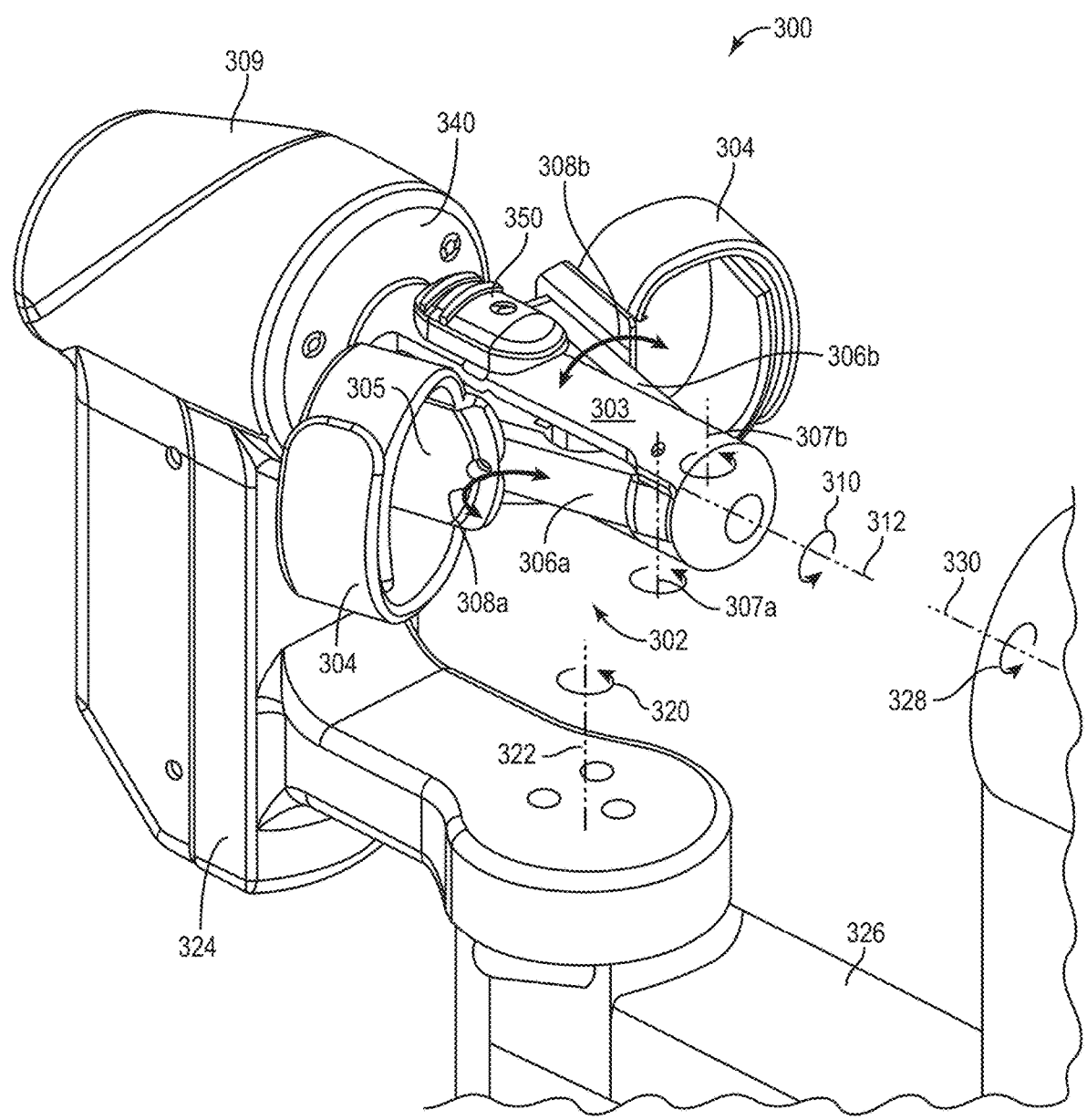
FIG. 3 is a perspective view of an example portion of a control input device which can include one or more features described herein, according to some implementations.

FIG. 3 is a perspective view of an example controller portion 300 of a control input device which can include one or more features described herein. In some implementations, the control input device can be part of a system in which user input provided via the control input device is used to control one or more controllable device functions. For example, the system can be a teleoperated system in which the control input device is, or is included in, a master device that controls a manipulator device (e.g., slave device). For example, controller portion 300 can be used as a portion of an input control device that is a control input device 210 or 212 as described above with reference to FIGS. 1 and 2, or portion 300 can be included in a different control device. In some implementations, the controller portion 300 includes one or more gimbal mechanisms.

Controller portion 300 includes a handle 302 which is contacted by a user to manipulate the control input device. In this example, the handle 302 includes two grips that each include a finger loop 304 and a grip member 306 (grip members 306a and 306b). The two grip members 306 are positioned on opposite sides of a central portion 303 of the handle 302, and the grip members 306 can be grasped, held, or otherwise contacted by a user's fingers. Each finger loop 304 is attached to a respective grip member 306 and can be used to secure a user's fingers to the associated grip member 306. In this example, finger contacts 305 can be connected or formed at the unconnected end of the grip members 306a and 306b to provide surfaces to contact the user's fingers. The user may also contact other portions of handle 302 while grasping the grip members 306.

Each grip member 306 and finger loop 304 can be moved in an associated degree of freedom 308 (e.g., 308a and 308b). In some examples, the grip members 306a and 306b are each coupled to the central portion 303 of the handle 302 at respective rotational couplings, allowing rotational movement of the grip members about grip axes 307a and 307b, respectively, with respect to the central portion 303. Each grip member 306a and 306b can be moved in an associated degree of freedom 308a about axis 307a and degree of freedom 308b about axis 307b, respectively, e.g., by a user contacting the grip members. For example, in some implementations the grip members 306a and 306b can be moved simultaneously in a pincher-type of movement (e.g., toward or away from each other). In various implementations, a single grip member 306 and finger loop 304 can be provided, or only one of the grip members 306 can be moved in the degree of freedom 308 while the other grip member 306 can be fixed with reference to the handle 302. For example, the positions of grip members 306a and 306b in their degrees of freedom can control corresponding rotational positions of an end effector or component thereof.

One or more grip sensors (not shown) can be coupled to the handle 302 and/or other components of the controller portion 300 and can detect the positions of the grip members 306a and 306b in their degrees of freedom 308. The grip sensors can send signals describing sensed positions and/or motions to one or more control circuits of the teleoperated system 100. In some modes or implementations, the control circuits can provide control signals to a manipulator device, e.g., manipulator system 104. For example, the positions of the grip members 306a and 306b in degrees of freedom 308a and 308b can be used to control any of various degrees of freedom of an end effector of the manipulator system 104, some examples of which are described herein.

Various implementations of the controller 300 can provide one or more active actuators (e.g., motors, voice coils, etc.) to output active forces on the grip members 306 in the degrees of freedom 308. For example, a sensor and/or actuator can be housed in central portion 303 or in housing 309 and coupled to the grip members 306 by a transmission. Some implementations can provide one or more passive actuators (e.g., brakes) or springs between the grip members 306 and the central portion 303 of the handle 302 to provide resistance in particular directions of the grips (e.g., movement in directions toward each other in degree of freedom 308).

Handle 302 is additionally provided with a rotational degree of freedom 310 about a roll axis 312 defined between a first end and second end of the handle 302. The roll axis 312 is a longitudinal axis in this example that extends approximately along the center of the central portion 303 of handle 302. Handle 302 can be rotated about axis 312 with respect to a base member of the controller portion 300, such as a base member that includes housing 309. For example, a user can rotate the grip members 306 and central portion 303 as a single unit around the axis 312, with respect to housing 309, to provide control of a manipulator device, such as an end effector of the manipulator system 104 or other element of the manipulator system.

One or more control input sensors (not shown) can be coupled to the handle 302 to detect the orientation of the handle 302 in the rotational degree of freedom 310. For example, the sensor can send signals describing the orientation to control circuits of the teleoperated system 100 which can provide control signals to the manipulator system 104 similarly as described above. For example, rotation of handle 302 in degree of freedom 310 can control a particular degree of freedom of an end effector of the manipulator system 104 that is different than a manipulator degree of freedom controlled by degree of freedom 308 of the grip members 306.

Some implementations of the controller portion 300 can provide one or more actuators to output forces on the handle 302 (including grip members 306 and finger loops 304) in the rotational degree of freedom 310. For example, a sensor and/or actuator can be housed in housing 309 and coupled to the handle 302 by a shaft extending through the central portion 303 of the handle 302.

In various implementations, the handle 302 can be provided with additional degrees of freedom. For example, a rotational degree of freedom 320 about a yaw axis 322 can be provided to the handle 302 at a rotational coupling between an elbow shaped link 324 and a link 326, where the elbow shaped link 324 is coupled to the handle 302 (e.g., at housing 309). In this example, yaw axis 322 intersects and is orthogonal to the roll axis 312. For example, yaw axis 322 can be similar to axis 232 shown in FIG. 2. Additional degrees of freedom can similarly be provided. For example, link 326 can be elbow-shaped and a rotational coupling can be provided between the other end of link 326 and another link (not shown). A rotational degree of freedom 328 about an axis 330 can be provided to the handle 302 at the rotational coupling. For example, axis 330 can be similar to axis 230 shown in FIG. 2. In some examples, the controller portion 300 can allow movement of the handle 302 within the workspace 114 of the user control system 102 with a plurality of degrees of freedom, e.g., six degrees of freedom including three rotational degrees of freedom and three translational degrees of freedom. One or more additional degrees of freedom can be sensed by associated control input sensors and/or actuated by actuators (motors, etc.) similarly as described above for the degrees of freedom 308 and 310, the sensors and actuators coupled to portion 300. In various implementations, sensors can sense positions of the handle in a degree of freedom, or sense orientations of the handle in a degree of freedom, or sense positions and orientations of the handle in multiple degrees of freedom. For example, positions in a translational degree of freedom and orientations in a rotational degree of freedom can be sensed by one or more control input sensors associated control input sensors. In some examples, a position in a translational degree of freedom and/or orientation in a rotational degree of freedom can be derived from rotations of components (e.g., links of a linkage) coupled to the handle 302 as sensed by rotational sensors. Some implementations can include linear sensors that can directly sense translational motion of one or more components coupled to the handle 302. In some implementations, each additional degree of freedom of the handle 302 can control a different manipulator degree of freedom (or other motion) of an end effector of the manipulator system 104.

In an example implementation, handle 302 is mechanically grounded, i.e., supported in space by a kinematic chain with an end stationary at mechanical ground, such as a floor, wall, or ceiling. For example, the housing 309 can be coupled to a mechanical linkage that is coupled to the ground or an object connected to ground, providing a stable platform for the use of the hand controller portion 300. For example, a grounded mechanical linkage can be connected to the base member, e.g., with one or more rotary couplings, ball joints, or other couplings, including linear joints. The mechanical linkage can provide six or more degrees of freedom to the handle 302. In some implementations, one or more links in the linkage can include links 324 and 326.

In some examples, the base member can be coupled to a serial kinematic chain, the proximal end of which is mechanically grounded. The kinematic chain can include multiple members or links that are rotatably coupled to one or more other members or links of the chain, e.g., by rotational or linear couplings. The rotational axes of the chain can be sensed and/or driven by sensors and/or actuators. Some implementations can provide additional actuated and/or sensed motion of the kinematic chain, e.g., about axes extending lengthwise through one or more members. In some implementations, multiple members of the kinematic chain form a gimbal mechanism that allows the handle 302 to be rotated about the rotational axes of the chain. In some implementations, the handle 302 can also be translated in at least three linear degrees of freedom allowed by the kinematic chain.

Various kinematic chains, linkages, gimbal mechanisms, flexible structures, or combinations of two or more of these can be used with the mechanically grounded hand controller in various implementations to provide one or more degrees of freedom to the hand controller. Some examples of such implementations are described in U.S. Pat. No. 6,714,839 B2, incorporated herein by reference.

In the described example, handle 302 includes one or more control switches 350, e.g., coupled to the central portion 303 or to mechanisms within central portion 303. For example, two control switches 350 can be positioned on opposite sides of axis 312, and/or additional control switches can be provided. In some examples, a control switch 350 has a portion that can slide parallel to the axis 312, e.g., as directed by a user's finger, or the control switch portion can be depressed. In some implementations, the control switch 350 can be moved to various positions to provide particular command signals, e.g., to select functions, options, or modes of the control console and/or control input device (e.g., a controlling mode or non-controlling mode as described herein), to command a slave device or other system in communication with the control input device, etc. In some implementations, one or more of the control switches 350 can be implemented as a button (e.g., depressed in a direction, such as perpendicular to the axis 312 or other direction), a rotary dial, a switch that moves perpendicular to the axis 312, or other type of input control. Control switch 350 can use electromagnetic sensors, mechanical switches, magnetic sensors, or other types of sensors to detect positions of the switch.

Handle 302 also includes a hand presence sensing system including one or more presence sensors that can detect the presence of a user's hand operating the handle, detect the user's hand approaching or leaving the handle, detect a hand approaching or leaving the handle as well as a presence of the user's hand operating the handle, etc. Various implementations of presence sensors are described below with respect to FIGS. 4-8.

One or more features described herein can be used with other types of control input devices. For example, controller portion 300 can be or be a portion of a mechanically ungrounded control input device which is free to move in space and is disconnected from ground. As used herein, a mechanically ungrounded control input device refers to a control input device that is unconstrained with respect to possible position and orientation motion in a working environment (e.g., an operating area or room). Also, such a control device is kinematically separated from the ground, e.g., not mechanically supported by a console, supports, or other object attached to the ground. In some implementations, a mechanically ungrounded control device may be in tethered or untethered connection with one or more associated components such as control processors, data sources, sensors, power supplies, etc. For example, the control device may be tethered, e.g., connected physically to these components via a cable or wire, or untethered, e.g., not physically connected to such components and in communication with the components via wireless communication signals.

In some examples, one or more handles similar to handle 302 and/or grip members 306 can be coupled to a mechanism worn on a user's hand and which is ungrounded, allowing the user to move grips freely in space. In some examples, the positions of the grips relative to each other and/or to other portions of the handle can be sensed by a mechanism coupling the grips together and constraining their motion relative to each other. Some implementations can use glove structures worn by a user's hand. Furthermore, some implementations can use sensors coupled to other structures to sense the grips within space, e.g., using video cameras or other sensors that can detect motion in 3D space. Some examples of ungrounded control input devices are described in U.S. Pat. No. 8,543,240 B2 (filed Sep. 21, 2010) and U.S. Pat. No. 8,521,331 B2 (filed Nov. 13, 2008), both incorporated herein by reference in their entireties.

Figure 4:
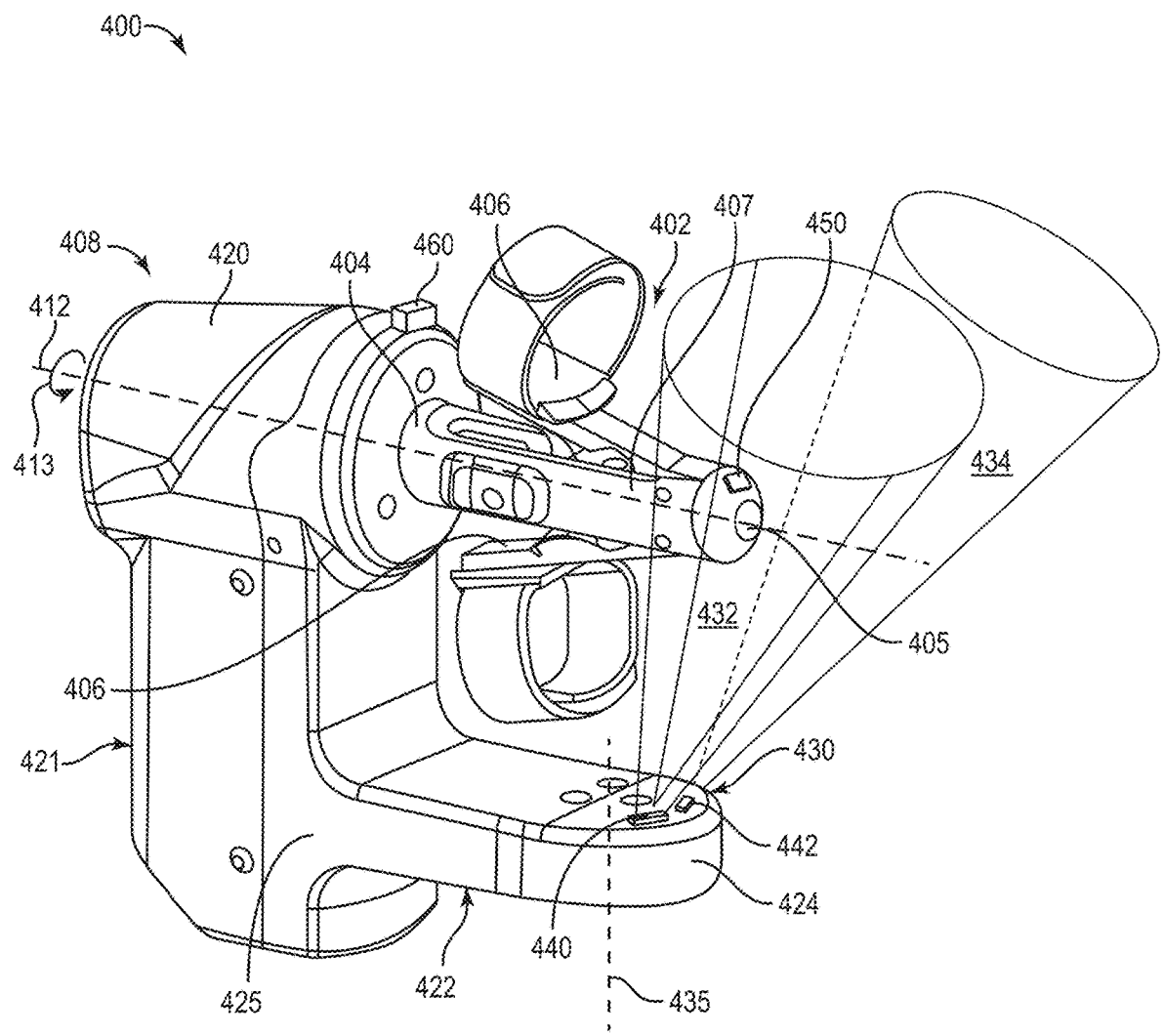
FIG. 4 is a perspective view of an example portion of a control input device including an example implementation of a presence sensing system, according to some implementations.
Figure 5:
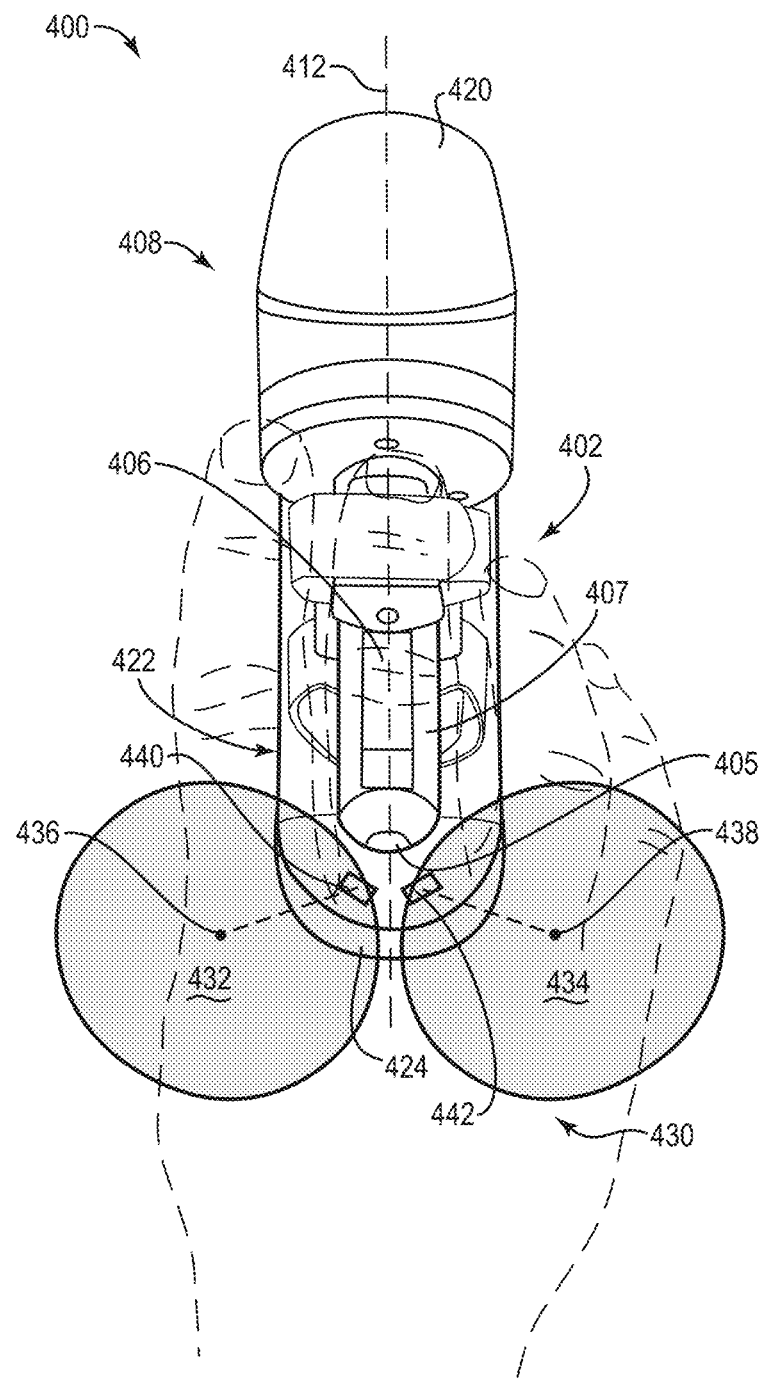
FIGS. 5 and 6 are a top view and a side view, respectively, of the example control input device of FIG. 4, according to some implementations.
Figure 6:
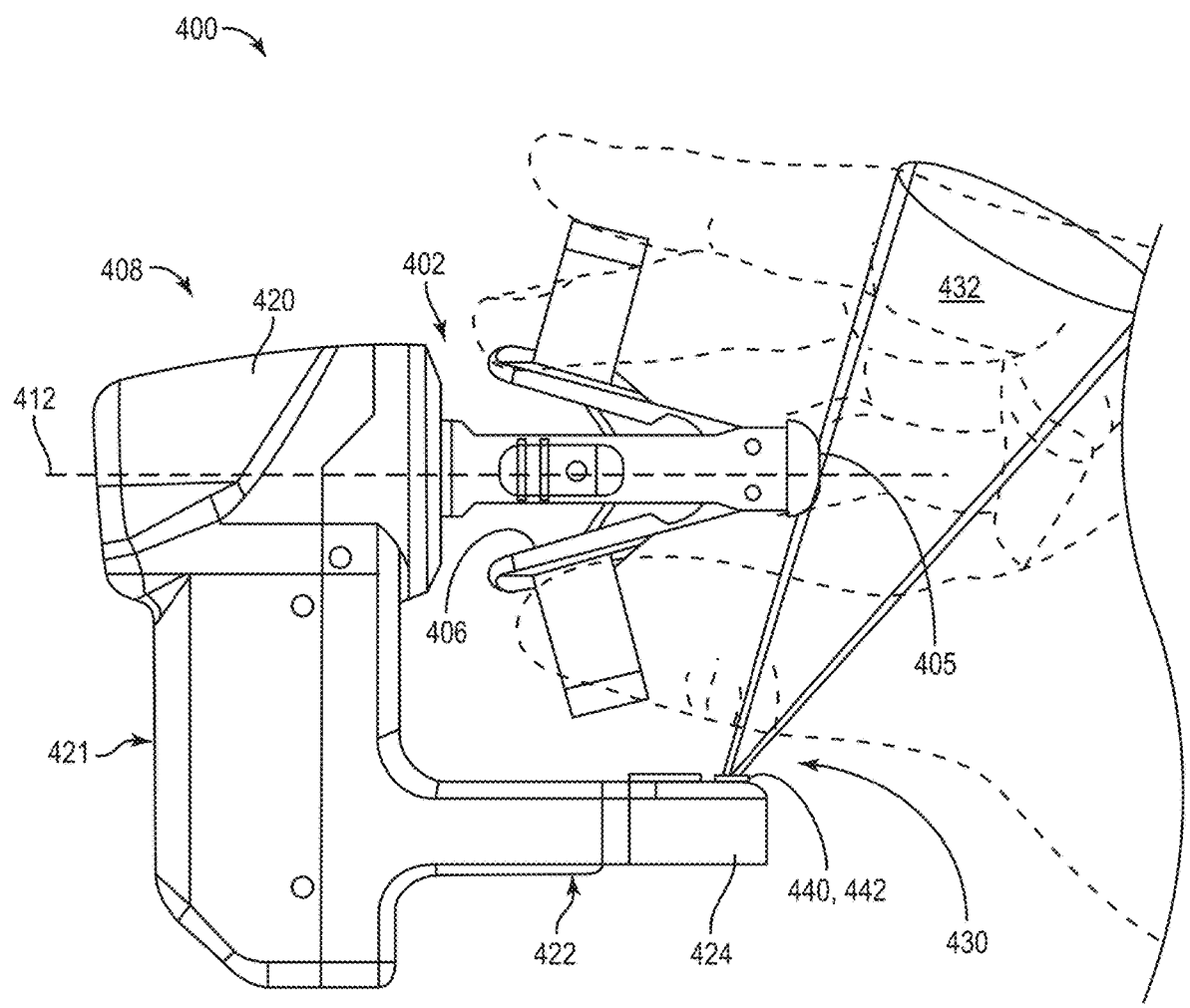

FIG. 4 is a perspective view of an example implementation of a controller portion 400 of a control input device including an example implementation of a presence sensing system. FIG. 5 is a top plan view of the controller portion 400, and FIG. 6 is a side elevational view of the controller portion 400.

In some implementations, the controller portion 400 can be implemented as the control portion 300 described above with respect to FIG. 3, or can be included in a different input control device.

Controller portion 400 includes a handle 402 (shown in cross section) coupled to a base member 408, which can be similar to handle 302 and housing 309 as described for FIG. 3.

Handle 402 includes a first end (proximal end) 404, a second end (distal end) 405 opposite the first end, and a central axis 412 defined between the first and second ends. A central portion 407 can extend between the proximal end 404 and distal end 405. Handle 402 (e.g., a roll member) can be rotated about central axis 412 in a roll degree of freedom 413 with respect to the base member 408. In some implementations, handle 402 can include the grip members 406 that are rotationally coupled to a central portion 407 that extends along the central axis 412, similarly as grip members 306 of FIG. 3. Central portion 407 is configured to be positioned between at least two fingers of a hand during grip of the handle by the hand, similarly as described for FIG. 3. One or more control input sensors (e.g., roll sensors) can be coupled to the controller portion 400 and detect the roll (rotary) orientation of handle 402 about axis 412. The roll sensors can send signals describing sensed orientations and/or motion to a control circuit of the teleoperated system 100. In some modes or implementations, the control circuit can provide control signals to the manipulator system 104. In some implementations, an actuator (e.g., motor) can be used to drive rotation of handle 402 about central axis 412.

Base member 408 is rotationally coupled to handle 402, allowing handle 402 to rotate about axis 412 with respect to the base member 408. Base member 408 can have a variety of shapes and can include portions or extensions in various configurations. In an example implementation, base member 408 is mechanically coupled to a ground such that handle 402 is mechanically grounded, e.g., via one or more links (such as links 324 and 326 as described above). In other implementations, base member 408 is mechanically ungrounded.

In the example of FIG. 4, base member 408 includes a first base portion 420, a second base portion 421, and a third base portion 422. First base portion 420 is rotatably coupled to handle 402. Second base portion 421 extends from the first base portion 420. In various implementations, second base portion 421 extends approximately orthogonally to the central axis 412 of handle 402 as shown, or can extend at other angles relative to the central axis 412. Third base portion 422 extends from the second base portion. In various implementations, third base portion 422 cab extend approximately parallel to a central axis 412 of handle 402, or can extend at other angles relative to the central axis 412. For example, a distal end (e.g., portion) 424 of parallel portion 422 can be rotationally coupled to another base member, similarly as described for FIG. 3.

Controller portion 400 includes a presence sensing system 430 that is coupled to the parallel portion 422 of the base member 408. Presence sensing system 430 includes one or more presence sensors that sense objects in one or more sensing fields in space. Herein, a "sensing field" can include multiple individual sensing fields, e.g., each individual sensing field provided by a corresponding one of multiple sensors. In some implementations, sensor(s) of the presence sensing system 430 detect a presence of an object in the sensing field. For example, the sensor can detect electromagnetic radiation (or ultrasonic wave, as described below) that is directed through space to the sensor by a presence of an object in the sensing field of the sensor, such as a hand. In response to detecting the object, the presence sensor generates one or more signals that are sent to a control circuit for the control input device. For example, in some implementations the signal can include a parameter, e.g., a value that indicates the detection of an object and/or corresponds to a variable distance between the object (e.g., hand) and the presence sensor (or other reference location). The parameter can also or alternatively indicate other characteristics, e.g., velocity of the object.

In the example of FIG. 4, presence sensors 440 and 442 (described below) are used and are positioned at the distal end (e.g., portion) 424 of the parallel portion 422 that extends parallel to the central axis 412. For example, the distal end 424 can be closer than the proximal end (e.g., portion) 425 of the parallel portion 422 to the distal end 405. In some implementations, the presence sensing system 430 can include one or more optional sensors at one or more other locations of the controller portion 400. In some examples, one or more optional sensors 450 are positioned at the distal end 405 of handle 402, as described below with respect to FIG. 7. In some implementations, one or more sensors 460 are positioned on the base portion 420 of the base member 408, as described below with respect to FIG. 8.

In some implementations, the presence sensor(s) use a direct linear view through space to detect a hand, such that at least a portion of the hand should be unobstructed in a linear view path to the sensor to allow detection. The presence sensors are placed such that components of handle 402 and controller portion 400 do not obstruct the sensing field. Thus, the example locations of placement for sensors 440, 442, 450, and 460 provide unobstructed sensing fields to detect at least a portion of a hand during its operation of the control input device, and/or to detect a hand near handle 402. In this example, the presence sensors are also placed so that a hand must be positioned within the sensing field as the hand approaches the handle (for detecting hand approach or proximity) and when the hand is in a position to operate the handle (for detecting hand presence in an operating position).

In some implementations, as shown in the example of FIG. 4, sensors 440 and 442 provide two individual sensing fields 432 and 434 (e.g., fields of view), respectively, directed to different regions of space near handle 402. In this example, sensing field 432 is directed to a region of space that is on a first side of the central axis 412 (e.g., on a first side of central portion 407 and grip members 406 of handle 402), and sensing field 434 is directed to a different region of space that is on a second side of the central axis 412 (e.g., on a second side of central portion 407 and grip members 406). For example, the different sides can be different sides of a vertical plane that extends through the central axis 412. For example, the vertical plane can be oriented in the vertical direction with reference to FIG. 4 or 6. In some implementations, the first side can be a left side of a vertical plane that extends through the central axis 412 and central portion 407, and the second side can be a right side of the vertical plane that extends through the central axis 412 and central portion 407, with respect to a user positioned on the side of distal end 405.

An example of sensing fields 432 and 434 positioned on the left and right sides, respectively, of central axis 412 as described above, which are provided by sensors 440 and 442 positioned on the parallel portion 422, is shown in FIG. 5. In this example, the sensing fields do not overlap, and the central axis 412 extends between the sensing fields 432 and 434 without entering or intersecting either of the sensing fields.

Additionally or alternatively, the sensing fields 432 and 434 can be positioned at least partially in front of handle 402 from a user's perspective, e.g., between distal end 405 of handle 402 and a user. For example, as shown in FIG. 5, the sensing fields 432 and 434 are positioned to the sides of the central axis 412 and are partially positioned in front of the distal end 405 such that center axes 436 and 438 of the sensing fields 432 and 434, respectively, are in front of the distal end 405 of handle 402.

In some implementations, as shown in FIG. 6, the sensing fields 432 and 434 are at least partially positioned in a spatial region extending past an end of handle 402. For example, the sensing fields 432 and 434 can be positioned at least partially in front of the distal end 405 of handle 402 (e.g., to either side or both sides of axis 412 as shown in FIG. 5), with respect to a user.

In some implementations, sensor 440 can provide sensing field 432 and sensor 442 can provide sensing field 434. In some implementations, a single sensor can provide multiple individual sensing fields, e.g., sensing fields 432 and 434 and/or additional sensing fields. In some implementations, a sensing field can be a combination of multiple individual sensing fields. In the implementation shown, the sensors of the presence sensing system, including sensors 432 and 434, are not located on a surface of the handle that is contacted by the hand during operation of the control input device, nor do they sense such contact of the user with such contacted surfaces of the handle.

Fingers of a hand operating handle 402 may contact grip members 406 as shown, such that the operating hand is present in at least one of the sensing fields 432 and 434. For example, the sensing field is positioned such that the hand is included in the sensing field in response to one or more fingers of the hand touching either of the two grip members.

The sensing field(s) are configured to include at least a portion of the hand in response to one or more fingers of the hand touching either of the two grip members 406. Thus, the position of the sensing fields 432 and 434 on the sides of central axis 412 in the example of FIGS. 4-6 allows these fields to sense portions of the user's hand while the hand operates the control input device. In some implementations, hand portions closer to the wrist can be sensed (e.g., a side of the palm portion of the hand) if fingers of the hand (or a portion of one of more fingers) are outside the sensing fields 432 and 434 during operation.

In some implementations, the left and right placement of the sensors can provide more robust sensing than a sensor that is centered to point directly at the distal end 405 or directly in front of distal end 405 (e.g., intersecting axis 412). For example, a disadvantage of some implementations of centered sensors is that it may be possible, in some hand grip configurations, for a centered sensing field to be in a gap between the users fingers and miss detection of the hand. The left and right placement allows the sensors to detect the regions to the sides of the grip mechanisms 406, e.g., without detecting the distal end 405. In some implementations, a single sensor pointed towards the distal end 405 can be used, e.g., if the sensing field of the sensor is sufficiently wide to detect the hand in various possible hand grip configurations.

In some implementations, as shown in FIGS. 4-6, at least a portion of the sensing field is located in an approach region or path of a hand when the hand moves toward the handle prior to operating the handle. For example, the hand enters one or more of the sensing fields as the hand approaches the handle with user intent to operate the handle. In some implementations, the sensing field has an orientation and/or size such that an object, such as a hand, can be sensed within as well as outside a particular designated region, e.g., sensed within or greater than a designated threshold distance as described herein.

The orientation, size, and/or shape of sensing fields 432 and 434 can be based on the type of sensors 440 and 442 that are used to detect a presence of a hand of a user. Some examples of types of sensors which can be used for sensors 440 and 442 are described below.

In some implementations, each sensing field 432 and 434 can be shaped as a cone. For example, the sensing field 432 can have a particular width at the sensor 440 and increases in width in a direction away from the sensor 440, and a similar sensing field 434 can be provided by sensor 442. Herein, the term "cone" or "conical" refers to an approximate cone shape, which does not necessitate an exact conical geometry, e.g., manufacturing tolerances, interference patterns, warps due to obstructions such as handle 402, or other allowances can be included in the conical sensing field. Furthermore, this term can refer to cones having circular cross sections, as well as or alternatively cross sections of other shapes, e.g., ellipses, ovals, rectangles, squares, triangles, etc. In some implementations, each sensing field 432 and 434 can be shaped as a cylinder, rectangle, or other shape. Each cone has a depth and volume limited by a sensing range of the associated sensor 440 or 442. In some implementations, the sensing field shape can be made wider or narrower, e.g., as appropriate to cover regions that are proximate to and/or intersected by the distal end 405 of handle 402. In some implementations, the sensing field can be limited to a particular size, e.g., depth and/or volume, that may be less than the sensor capability of the sensor. For example, the depth can be limited to a particular distance from the sensor at which the sensor can detect objects in its sensing field. In some examples, the sensing field can be limited, e.g., in depth and/or volume, so that other portions or components of the control input device (or components of a system including the control input device) are not potentially erroneously detected as hands.

In some implementations, the sensing fields 432 and 434 can partially overlap. For example, in an alternative implementation of FIG. 5, the sensing fields 432 and 434 can overlap in front of the distal end 405 of handle 402 such that central axis 412 extends through both sensing fields 432 and 434.

In some implementations, handle 402 is proximate to and external to (e.g., outside) the sensing fields 432 and 434. In some examples, handle 402 is not present in and does not extend into the sensing fields. With some types of sensors that detect electromagnetic radiation signals reflected from an object in the sensing field, the handle being external to the sensing fields allows only new objects present in the sensing field to reflect the signals.

In some implementations, a portion of handle 402 can extend into one or more of the sensing fields of the presence sensing system, e.g., into sensing fields 432 and 434 such that handle 402 intersects one or more of the sensing fields. For example, the distal end 405 of handle 402 can extend into one or both sensing fields 432 and 434. With some types of sensors, reflected signals caused by the components of handle 402 can be normalized such that such handle components 402 are ignored and new objects located within the sensing field are detected by the time of flight sensors.

The sensing fields 432 and 434 have spatial positions that are fixed with respect to the central axis 412 of handle 402, e.g., fixed with respect to the spatial position of handle 402. In some examples, sensors 440 and 442 that emit the sensing fields 432 and 434 are positioned on the parallel portion 422 of the base member 408 that is fixed with respect to central axis 412. Thus, the sensing fields 432 and 434 can sense these spatial regions relative to the central axis 412 regardless of the position of the central axis 412 of handle 402 in space, and regardless of the movement of handle 402 in its degrees of freedom. For example, if handle 402 can rotate about axis 435 at a rotary coupling with another link (similar to axis 322 in FIG. 3), the sensing fields 432 and 434 rotate with handle 402 about axis 435. Handle 402 may also rotate about the central axis 412, and this rotation is relative to the central axis 412, sensing fields 432 and 434, and base member 408.

The size (e.g., volume and/or depth) of the sensing field of each individual sensor 440 and 442 is typically limited. The use of two sensing fields 432 and 434 allows the sensing field of the presence sensing system 430 to be extended to a larger total size (e.g., large volume and/or larger range) than when using a sensing field of a single sensor. The total sensed field in this implementation is extended to cover the regions on the sides of the central axis 412 of handle 402.

In some implementations, portions of the sensing fields 432 and/or 434 can be blocked or adjusted in size or dimensions, e.g., by selecting particular settings of the sensors emitting the sensing fields. In some implementations, one or more of the sensors 440 and 442 may be physically masked to block portions of the standard sensing field of the sensor from being sensed. For example, this can prevent the sensor from detecting objects such as grip members 406 or other components of handle 402 which are to be ignored.

In some implementations using multiple sensing fields, as in the example of FIG. 4 using sensing fields 432 and 434, a hand (or other object) can be detected in one of the sensing fields and may not be detected in the other sensing field(s). In some implementations, if a hand is detected in one sensing field and not in the other sensing field, then a detection is made, e.g., detection of an object is considered to have occurred. In other implementations, a detection of a hand requires that the hand be detected in both (or all) sensing fields.

Detection of a hand by the presence sensing system can occur when the hand contacts the control input device, e.g., during operation of the control input device by the hand, and/or can occur when the hand does not contact the control input device, e.g., on approach or departure of the hand from the control input device. In some implementations, multiple types of hand detection can be performed by the presence sensing system, e.g., a first type of detection of a hand approaching the control input device, and a second type of detection of a hand in an operating position where the control input device can be operated by the hand.

An advantage of the sensing fields 432 and 434 in the configuration of FIGS. 4-6 is that these fields are oriented such that a user's hand enters and/or is positioned within one or both of the sensing fields as the hand approaches handle 402, e.g., to operate the handle. Thus, presence sensing system 430 can detect the presence of a hand before it has contacted handle 402 (including contacting grips 406 or central portion 407), and/or after it has released contact with handle 402. In some implementations, the sensing system 430 can detect the hand before (or after) it contacts any part of the control input device portion 400. A system can use non-contact hand detection to, for example, enable particular associated functions of the control input device (e.g., powering up particular systems), track the hand to determine a trajectory of the hand and anticipate contact with the handle, etc., some examples of which are described below.

The configuration of the sensing fields 432 and 434 as shown in FIGS. 4-6 also or alternatively senses the presence of a hand operating the handle 402. For example, while a hand is grasping the two grip members 406, the hand extends into one or both sensing fields 432 and 434 on the sides and to the front of handle 402. This sensing field configuration can be used with any control input device of the system without changes needed for operation of handle 402 by a left hand or a right hand, since both left and right sides of central axis 412 are sensed (e.g., hand presence may be more easily detected on a particular side of the central axis 412 depending on whether the left or right hand is operating handle 402). The detection of the hand occurs at any rotational position of handle 402 about central axis 412, since a portion of the hand extends into one or both sides of handle 402 where sensing fields 432 and 434 are present at any such rotational position. Furthermore, a portion of the sensing fields 432 and 434 extends below the distal end 405 of handle 402 as shown in FIG. 6, allowing the sensors 440 and 442 to sense finger(s) (e.g., a thumb) of the user's hand which may extend below the central axis 412 in several positions of the handle 402 about central axis 412.

The sensing field(s) of described implementations are advantageous compared to contact sensors or sensors detecting presence on or very near a handle surface, since such sensors may not detect a hand when fingers of the hand are lifted away from the grip members 406 (e.g., within finger loops) during operation of handle 402, when fingers change position during operation (e.g., such that only finger tips or other finger portions contact the handle), and/or when fingers change position and rotate handle 402 to a rotational position about axis 412 that is not within the sensing range of the sensors. For example, in some control system implementations, fingers of the hand may be adjusted by the user to obtain a grasping position that causes the control input device to match its position and orientation to a controlled manipulator device such as an instrument end effector. Contact sensors have to sense many surfaces over a large surface area of handle 402 to sense such different hand positions, and such sensors may not be able to detect some hand positions. Thus, a user could still be controlling the manipulator device and desire to stay in the controlling mode between control input device and manipulator device, but a system having such contact sensors may not sense the user's contact in cases as just described and may deactivate the controlling mode.

In some implementations, detections from multiple sensors and/or sensing fields, such as sensing fields 432 and 434, can be used in combination to detect a hand of a user. For example, measured distance and/or velocity detected from multiple sensors can be used in various implementations for detection. In first example implementations, position values (e.g., distance values) describing a position of a detected object (such as a hand) in sensing fields can be used. For example, if both of two sensors 440 and 442 measure distance values of a detected object that meet a threshold (e.g., the object is detected at a distance from the reference location that is below a distance threshold), then a hand is considered to be detected, else a hand is not detected. In a different implementation, if one of the measured distance values meets the threshold, then a hand is considered to be detected, else a hand is not considered detected. In some implementations, different distance thresholds can be used. For example, a first distance threshold that is closer to the handle can be used to detect that a hand is contacting and/or operating the handle, and a second distance threshold that is further away from the handle than the first distance threshold can be used to detect nearby presence of the hand, e.g., detecting a hand that is not contacting the handle, and/or detecting whether the hand may be approaching or departing the handle, etc. In some examples, detection of nearby presence can be used to alert the system that a hand may soon operate the handle, activate other associated functions of the system, etc., some examples of which are described below.

In additional example implementations, the velocity of an object sensed by the sensors can be used. For example, if both of two sensors 440 and 442 sense a hand and both sensors measure a velocity of the hand that meets (e.g., is below) a velocity threshold, then a hand is considered to be detected, else a hand is not considered detected. In a different implementation, if both sensors sense a hand and one of the measured velocity values meets the threshold, then a hand is considered to be detected, else a hand is not considered detected.

In additional example implementations, a combination of position (e.g., distance) and velocity of an object sensed by the sensors can be used. For example, if both of two sensors 440 and 442 measure a distance that meets a distance threshold and a velocity that meets a velocity threshold, then a hand is considered to be detected, else a hand is not detected. In a different implementation, if both the sensors measure a distance that meets the distance threshold or a velocity that meets the velocity threshold, then a hand is considered to be detected, else a hand is not detected. In a different implementation, if one of the measured distance values meets the distance threshold and one of the velocity values meets the velocity threshold, then a hand is considered to be detected, else a hand is not detected. Other variations and permutations can be used. In some implementations, more than two sensors and/or sensing fields can be used, allowing additional combinations of distance and/or velocity detection (relative to thresholds) by all or subsets of the sensors or sensing fields to be used to determine whether a hand is considered to be detected.

In some implementations using multiple (e.g., two) sensing fields, an object (e.g., a hand) may be detected in one of the sensing fields and not detected in another sensing field. In some implementations, a detection of a hand requires that the hand be detected in multiple (or all) sensing fields of the control input device. In other implementations, if a hand is detected in one sensing field and not in the other sensing field, then a detection is considered to have occurred. For example, in some implementations, only one of the sensing fields may be able to detect a hand due to different hand postures relative to sensor field placement relative to the handle. In some examples, on a right-hand control input device, a right sensor (e.g., sensor 442 of FIG. 5) may detect the right hand and the left sensor (e.g., sensor 440 of FIG. 5) may not detect the right hand, and vice-versa for a left-hand control input device. If an object is detected only by one particular sensor (e.g., the right sensor on the right-hand control input device, or the left sensor on the left-hand control input device), such a system can be configured to indicate that a hand detection has occurred.

In some implementations, additional sensors can be provided (e.g., two or more right sensors 442 and two or more left sensors 440 on each control input device). In some examples, both right sensors must sense the hand for it to be considered a hand detection. This allows redundancy in the detection and sensor fault detection.

Sensors 440 and 442 are located on the parallel portion 422 of the base member 408 and not on the distal end 405 of handle 402, allowing sensor electronics to be more easily housed, powered, and/or communicated with (e.g., via physical connectors and/or wires) on the base member 408 rather than on the rotating end of the smaller handle 402.

In various implementations, various types of sensors 440 and 442 can be used, e.g., non-contact sensors that sense an object in a sensing field. These sensors may provide more robust sensing than contact sensors in some implementations, e.g., they can sense a hand regardless of whether the hand is wearing a glove or is wet/dry, and they are more tolerant to nearby electric fields, magnetic fields, or energy output.

In various implementations, the sensors 440 and 442 can sense energy reflected by an object in the field (e.g., optical time of flight, reflected laser, or ultrasound sensors), sense energy radiated by an object in a sensor field (e.g., heat energy in the infrared spectrum), or sense other physical quantities (e.g., physical pressure, electrical capacitance change, etc.). The energy or other physical quantity can be detected directly (e.g., an imaging camera) or indirectly by an effect it causes (e.g., a thermopile sensor).

For example, in some implementations, electromagnetic sensors (e.g., optical sensors, infrared sensors, etc.) can be used, which are able to detect any of various ranges of wavelengths of electromagnetic radiation, including visible light, infrared light, etc. In some examples, an electromagnetic sensor includes an emitter that emits a electromagnetic signal in the sensing field, and a detector that detects the electromagnetic signal (or a portion thereof) reflected from an object in the sensing field. For example, sensors 440 and 442 can be optical time-of-flight sensors that detect an object by measuring a position of the object that is the distance between the sensor and the object in the sensing field of the sensor, based on a measured time difference between the emission of an electromagnetic signal and the return of the electromagnetic signal to the sensor after it has been reflected by the object. Since the time-of-flight sensor can detect the distance of a hand to the sensor, the system can determine the direction of movement of a hand by continually determining the distance of sensed objects. In this way, the sensor can detect whether a hand is approaching the handle 402 or is moving away from the handle 402. In some implementations, this detection can be used to determine whether the user intends to operate the control input device, e.g., an approach direction toward the handle indicates such an intent. In some implementations, if it is determined that the user is not intending to operate the control input device, then some system components are not provided power (e.g., displays do not provide visual output, motors are not powered, etc.) until such intent is detected via a detected hand direction toward the handle.

Furthermore, a velocity of the detected object can also be determined in some implementations. In some examples, velocity can be determined based on a difference of detected positions (e.g., distances to reference location) of the object over time, indicating distance moved by the object over time. For example, the velocity can be used to determine user intent to operate the control input device. In some examples, the direction of the detected object is indicated by the determined velocity, e.g., a positive velocity indicates that the object is moving away from the control input device and a negative velocity indicates movement toward the control input device. If, for example, the detected object is moving away fast (e.g., a large positive determined velocity that exceeds a velocity threshold), the system can determine to exit controlling mode based on the velocity, irrespective of position (e.g., distance) of the object from the control input device or sensor. If the detected object moves slowly away (e.g., a small positive determined velocity that is less than the velocity threshold), then a position (e.g., distance) of the object can also be used to determine whether to exit controlling mode (e.g., a position outside a distance threshold to a handle reference location can cause to exit controlling mode). In some examples, a faster velocity can indicate stronger user intent, and/or can be used to determine whether to continue to monitor hand positions to determine such user intent. For example, if a slower velocity of the object (e.g., hand) is detected and the hand is a threshold distance away from the reference location (e.g., a threshold distance from the sensor detecting the hand, from the handle, or from another reference location), the system can wait and sense more data related to object position or velocity before making a determination that the user intends to operate the control input device.

In some implementations, one or more thermopile sensors can be used. A thermopile sensor includes a detector that detects infrared radiation emitted by objects located in the associated sensing field of the sensor. The sensor detects thermal changes, e.g., a differential temperature change, from the presence of objects of different temperatures in its sensing field. The infrared radiation emitted by the hand is typically much stronger (warmer) than other objects or components that may be located in the sensing field, e.g., portions of the handle in some implementations. In some implementations, portions of the handle that may radiate greater amounts of heat, such as an amount of heat within a threshold range of the lowest estimate of heat from a hand, can be positioned external to the sensing field.

The sensing field of a thermopile sensor can be a cone or other shape similarly as described above. A thermopile sensor can be placed at any of a variety of locations on the handle 402, base member 408, and/or other attached links. For example, one or more thermopile sensors can be located at any of the locations of the presence sensors and provide the sensing fields shown in FIGS. 4-8.

In some implementations, sensors 440 and/or 442 are thermal imaging cameras (e.g., thermographic cameras). For example, a thermal imaging camera can sense infrared radiation from warmer temperatures located in the sensing field of the camera, and provide data based on the sensed radiation that can be processed into two-dimensional (2D) images. Thus, the thermal imaging camera detects the presence of body portions such as a hand located in the sensing field of the thermal imaging camera. In some implementations, the sensing field of the thermal imaging camera is directed over a region that encompassed both sensing fields 432 and 434 shown in FIGS. 4-6. In some implementations, one or more components of the handle 402 can be located in the sensing field of the thermal imaging camera, such as the distal end 405 of the handle. For example, the heat from such components can be ignored by the system, and the heat emitted from an object such as a hand located in the sensing field is distinguishable by typically being greater. In some implementations, a detected object that is not a component of the system and which is detected to emit lower than a threshold amount of heat (as associated with a hand) is ignored as being an object that is not a hand. One or more thermal imaging cameras can be located at any of the locations of the presence sensors and provide the sensing fields shown in FIGS. 4-8.

A thermal imaging camera can sense and store successive frames or captured images of the sensing field, allowing the camera to sense of the direction of motion of sensed objects over time. By analyzing such successive frames, the system can determine whether a hand is moving toward the handle 402 or away from the handle 402. Furthermore, a velocity of the detected object (which can include direction of movement) can also be determined in some implementations, similarly as described above for the time of flight sensor.

In some implementations, an infrared sensor can emit an infrared beam in its sensing field at an object, and detect the beam reflecting from a surface of an object in the sensing field to detect the object. In some implementations, an electromagnetic sensor can detect a magnitude of a reflected beam of electromagnetic radiation to determine a distance to the sensor of a surface which reflected the beam (e.g., the greater the magnitude, the smaller the distance to the object).

In some implementations, one or more ultrasonic sensors can be used in the presence sensing system. An ultrasonic sensor emits an ultrasonic wave which to an object and is reflected from the object. The sensor receives the reflected wave, and the distance from the sensor to the object is determined based on the time of travel of the wave. In some implementations, an ultrasonic sensor can detect magnitudes of reflected sonic pulses to indicate distance of the sensor element from the sensor or sensor array (the lower the reflected magnitude, the longer the distance). An ultrasonic sensor can be located at any of the positions on the control input device described herein in FIGS. 4-8. In some implementations, ultrasonic sensors may have larger, less well-defined sensing fields than optical time-of-flight sensors, such that a single sensor can be used to sense a sensing field around the handle 402 to detect user presence, e.g., a sensing field that includes the sensing fields 432 and 434 shown in FIGS. 4-6.

In some implementations, one or more contact sensors can be used, which detect the presence of the user's hand when the hand physically contacts the sensor or a surface physically connected to the sensor. For example, capacitive or resistive sensors can be used, which measure the change in capacitance or resistance, respectively, on the control input device when the hand contacts the sensor (or when the hand is very near to the sensor, e.g., for capacitive sensors). Some types of contact sensors can detect energy from the hand (e.g., infrared sensors that sense only within contact range). In some examples, contact sensors can be located as close as possible to the distal end 405, and/or can be located on portions of grip members 406 of the controller portion 400. In some implementations, a capacitive ring sensor can be provided around a portion of the controller portion 400. For example, the ring sensor can run along the curved surface around the base portion 420 of the base member 408, e.g., near sensor 460. Such a ring sensor senses a change in capacitance when the hand is very near the ring, e.g., when fingers of the hand contact grip members 406.

In some implementations, one or more sensors of the presence sensing system can perform processing on detection signals and provide processed signals to a control circuit of the system (e.g., a processor). For example, a sensing system can detect the positions of a hand or other object over time and determine a direction of the object relative to a reference location, and/or determine a velocity of the object, and send parameters or values describing the direction and/or velocity to a control circuit.

One or more of the sensors described herein can be implemented using an integrated circuit sensor that includes, for example, a sensing element, signal conditioner, analog to digital converter (ADC), math engine to calculate sensed characteristics (e.g., sensed object temperature for a thermopile sensor), etc.

Figure 7:
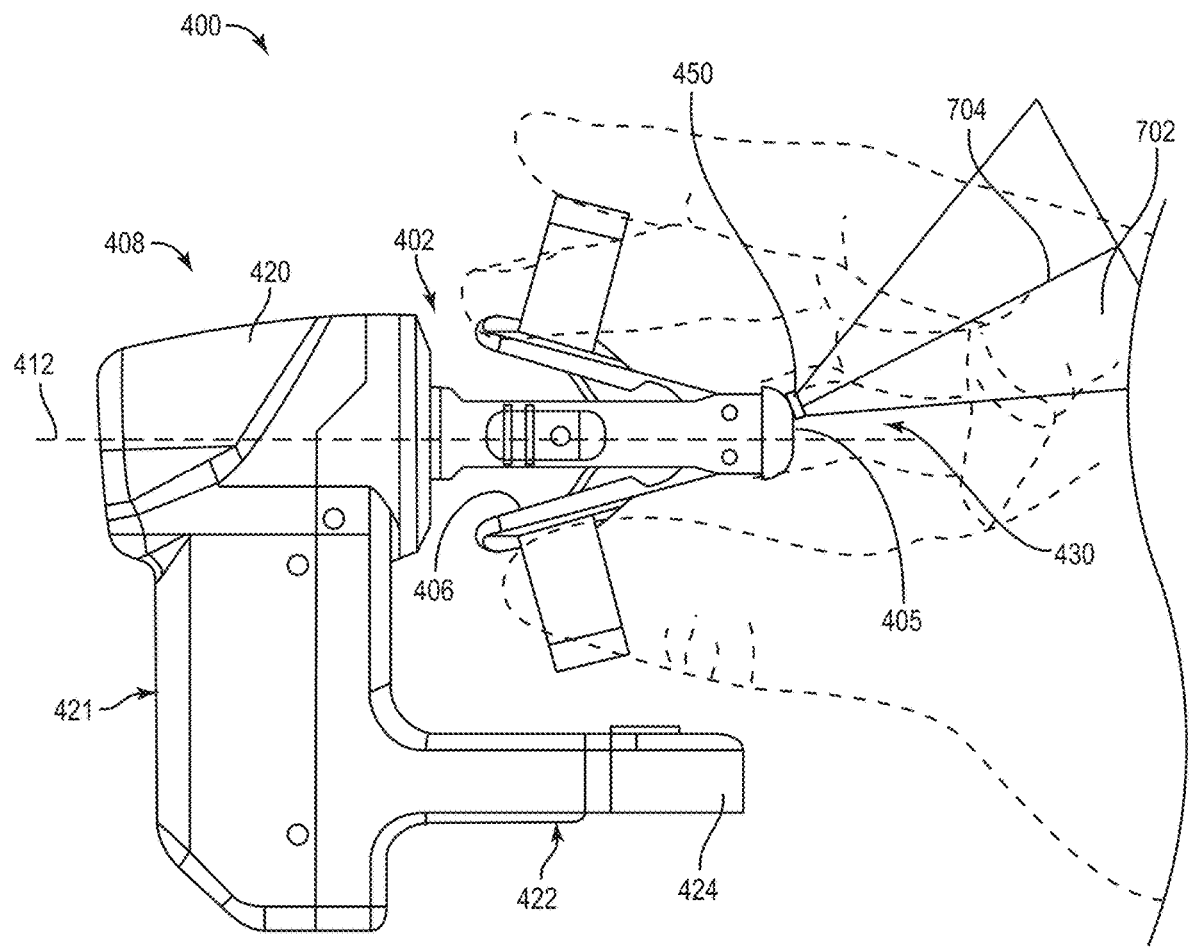
FIG. 7 is a side elevational view of the example control input device of FIG. 4 in which a presence sensor is located at a distal end of a handle, according to some implementations.

FIG. 7 is a side elevational view of controller portion 400 of the control input device including an example implementation of a presence sensing system in which the presence sensors are located at the distal end of the handle. In this example, presence sensor 450 as shown in FIG. 4 is provided at the distal end 405 of handle 402.

Sensor 450 senses objects in a sensing field 702. In some implementations, as shown in the example of FIG. 7, sensing field 702 is directed (e.g., away from handle 402) to a region of space that is at least partially in front of the distal end 405 of handle 402 with respect to viewpoint of a user operating handle 402. In some implementations, sensor 450 detects a portion of a palm or other non-finger portion of a hand within the sensing field 702. In some implementations, sensor 450 detects fingers and/or other portions of a hand that are operating the handle, e.g., with fingers contacting grip members 406 (example shown in dashed lines in FIG. 7). In some implementations, sensor 450 can detect the approach of the hand toward the handle 412, e.g., sensing field 702 extends beyond the distal end 405 to a region of space in front of the distal end 405 similarly as described above for other implementations.

In various implementations, the sensing field 702 can be directed on one side of a horizontal plane extending through the central axis, e.g., above such a horizontal plane as shown in FIG. 7, and central axis 412 extends below the sensing field 702 without entering or intersecting the sensing field. In some implementations, the sensing field 702 can extend below such a horizontal plane, or the sensing field 702 can be intersected by such a horizontal plane.

In some implementations, the sensing field 702 can be centered along the central axis 412 with reference to the view shown in FIG. 5. For example, the sensing field 702 can be bisected by a vertical plane extending through the central axis 412 orthogonally to the horizontal plane described above. In some implementations, the sensing field 702 can be directed at least partially to one side (e.g., the left or right) of the vertical plane, with reference to the view shown in FIG. 5. For example, the directed side is where a palm or other portion of the hand is expected to consistently be when operating the control input device. In some implementations, a left or right direction can accommodate one of a left-handed or right-handed use of the control input device, in which the operating hand is more reliably sensed on one side of the vertical plane.

The depth of the sensing field 702 (indicated by line 704) from the sensor 450 can be based on the type of sensor used. It extends sufficiently to detect a portion of a hand that is operating the control input device, e.g., with fingers engaged with grip members 406 in this example. In some implementations, portions of the sensing fields 432 and/or 434 can be blocked or adjusted in size or dimensions, e.g., by selecting particular settings of the sensor 450.

The sensing field 702 has a position that is fixed with respect to handle 402 and changes with respect to base member 408, due to the sensor 450 being positioned on the distal end 405 of handle 402 such that the sensor 450 rotates with the handle about axis 412.

In some implementations, multiple sensors can be provided at the distal end 405. For example, two sensors in the approximate location of sensor 450 can provide left and right sensing fields on left and right sides of axis 412, similarly to the sensors 440 and 442 as shown in FIG. 5.

Sensor 450 can be any of a variety of types of sensors, similarly as described above with respect to FIG. 4. For example, sensor 450 can be an electromagnetic time-of-flight sensor, thermopile sensor, thermal imaging camera, infrared sensor, ultrasonic sensor, etc.

In some implementations, sensing field 702 can be shaped as a cone. For example, the sensing field can have a particular width at the sensor 450 and extend in width in a direction away from the sensor 450. In some implementations, sensing field 702 can be shaped as a cylinder, rectangle, or other shape similarly as described above. In some implementations, the cone shape can be made wider or narrower.

In some implementations, handle 402 is external to the sensing field 702, e.g., handle 402 does not extend into the sensing field. In some implementations, a portion of handle 402 can extend into the sensing field 702, e.g., such that a portion of handle 402 intersects the sensing field. For some types of sensors, reflected signals caused by such components of handle 402 can be normalized such that such handle components are ignored and new objects located within the sensing field are detected by the sensor 450.

The sensing field 702 in the configuration of FIG. 7 can be oriented such that a user's hand enters the sensing field as the hand approaches handle 402, e.g., to operate the handle. Thus, presence sensing system 430 can detect the presence of a hand before it has contacted handle 402 (including contacting grips 406 or central portion 407). In some implementations, the sensing system 430 can detect the hand before it contacts any part of the controller portion 400.

The configuration of the sensing field 702 effectively senses the presence of a hand operating handle 402. For example, while a hand is grasping the two grip members 406, one or more portions of the hand, such as the palm, are present in sensing field 702. This sensing field configuration can be used with a control input device of the system without changes needed for operation of handle 402 by a left hand or a right hand. The detection of the hand occurs at any rotational position of the handle about axis 412, since a portion of the hand extends into sensing field 702 at any such rotational position.

The sensing field(s) of described implementations are advantageous compared to contact sensors or sensors detecting presence on or very near a handle surface, since such sensors may not detect a hand in various operating conditions similarly as described.

Figure 8:
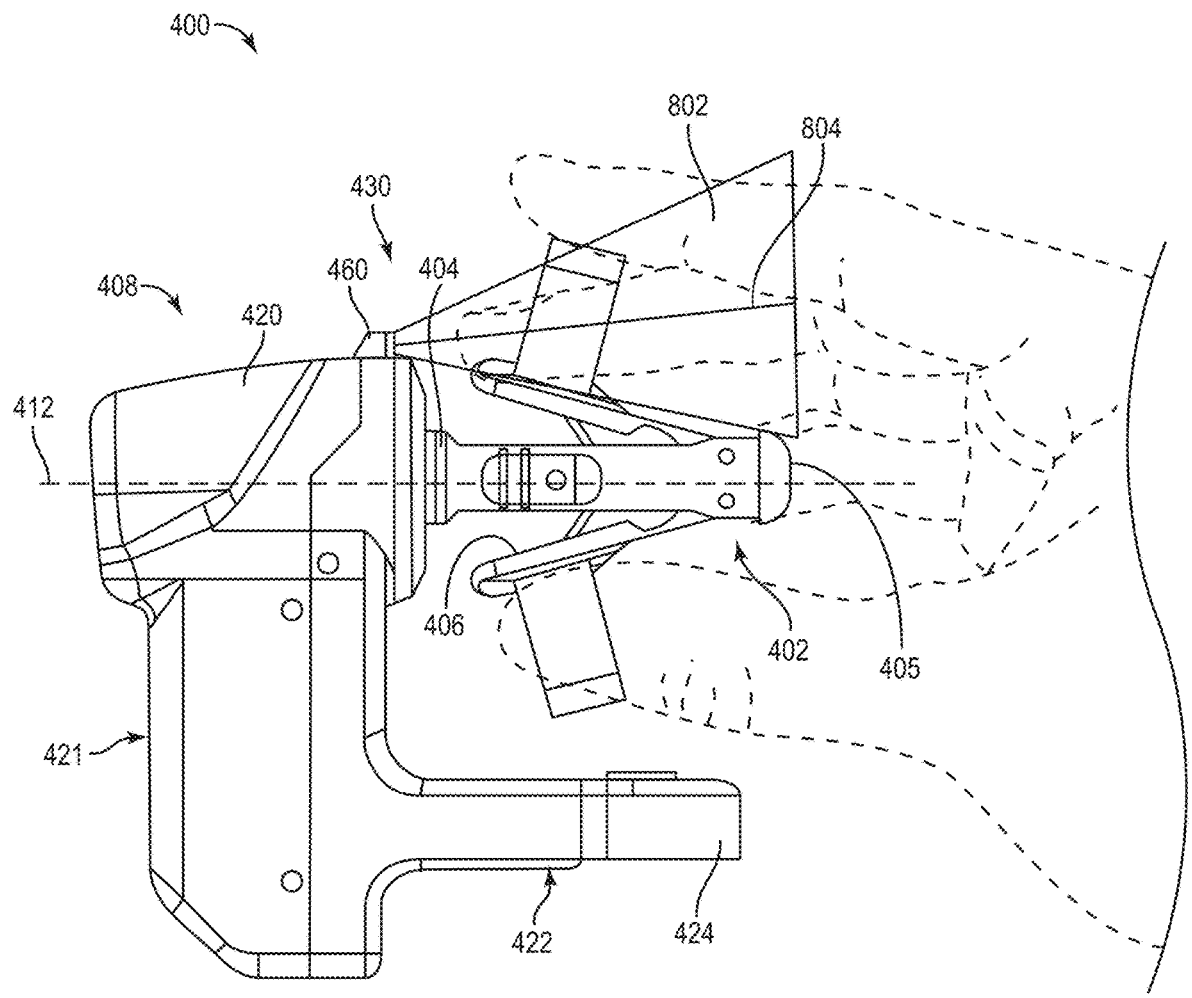
FIG. 8 is a side elevational view of the example portion of a control input device of FIG. 4 in which a presence sensor is located at a base member end of the handle, according to some implementations.

FIG. 8 is a side elevational view of controller portion 400 of the control input device including an example implementation of a presence sensing system in which one or more presence sensors are located at the base member end of handle 402 of the controller portion.

In this example, sensor 460, also shown in FIG. 4, is provided at the base portion 420 of the base member 408 of handle 402. For example, sensor 460 can be located at or near a side of the base portion 420 that is near to the proximal end 404 of handle 402, allowing the sensor 460 to provide a sensing field that encompasses at least a portion of handle 402. In this example, the sensor 460 is placed on top of base portion 420 with reference to the view of FIG. 8. In some implementations, sensor 460 can be placed on a different side of the base portion, e.g., at a bottom of base portion 420, or a different side of base portion 420.

Sensor 460 senses objects in a sensing field 802. In some implementations, as shown in the example of FIG. 8, sensing field 802 is directed (e.g., toward the operating hand), to a region of space that is located above a horizontal plane intersecting the central axis 412 of handle 402, with reference to the view of FIG. 8. The central axis 412 extends below the sensing field 802 without intersecting the sensing field 802. In some implementations, sensor 460 detects fingers and/or other portions of a hand within the sensing field 802. In some implementations, sensor 460 detects a portion of a hand operating the handle, e.g., detecting fingers contacting one or more grip members 406 (example shown in dashed lines in FIG. 8). In some implementations, sensor 460 can detect the approach of the hand toward handle 402, e.g., sensing field 802 extends beyond the distal end 405 to a region of space in front of the proximal end 405 and/or to the left and right of the central axis 412 similarly as described above for other implementations.

In some implementations, the sensing field 802 can extend below such a horizontal plane, e.g., using sensor 460 placed on a top side of base portion 420 to direct the field lower or downward (with reference to the view of FIG. 8), and/or by using a sensor placed on a bottom side, left or right side, or edge of base portion 420. Such a lower sensing field can detect fingers in a lower region, e.g., fingers (e.g., thumb) contacting or near the lower grip member 406 shown in FIG. 8. In some implementations, the sensing field 802 can be centered along the central axis 412 with reference to the view as shown in FIG. 5. For example, the sensing field 802 can be bisected by a vertical plane extending through the central axis 412 orthogonally to the horizontal plane described above. In some implementations, the sensing field 802 can directed at least partially to one side (e.g., the left or right) of the vertical plane, with reference to the view shown in FIG. 5. For example, the directed side can be a region where a palm or other portion of a hand is expected to consistently be when operating the control input device. In some implementations, a left or right direction can accommodate one of a left-handed or right-handed use of the control input device, in which the operating hand is more reliably sensed on one side of the vertical plane.

The depth of the sensing field 802 (indicated by line 804) from the sensor 450 can be based on the type of sensor used. It extends sufficiently to detect a portion of a hand that is operating the control input device, e.g., with fingers engaged with grip members 406 in this example. In some implementations, portions of the sensing field 802 can be blocked or adjusted in size or dimensions, e.g., by selecting particular settings of the sensor 460.

The sensing field 802 has a spatial position that is fixed with respect the central axis 412 of handle 402. Thus, the sensing field 802 can sense the same spatial region relative to the central axis 412 regardless of the position of the central axis 412 of handle 402 in space. The rotational orientation of handle 402 about central axis 412 varies with respect to the sensor 460 and may cause different portions of the handle 402 and the hand operating handle 402 to be present within the sensing field 802. The sensing field 802 can be made of sufficiently size and width such that a portion of the hand is always present within the sensing field 802, regardless of rotational orientation of handle 402 about central axis 412.

In some implementations, multiple sensors can be provided on the base portion 420. For example, two sensors in the approximate location of sensor 460 can provide left and right sensing fields on left and right sides of axis 412, similarly to the sensors 440 and 442 as shown in FIG. 5. In some implementations, sensors can be provided at multiple locations around the base portion 420 to cover different spatial regions that each include a different portion of handle 402.

Sensor 460 can be any of a variety of types of sensors, similarly as described above with respect to FIG. 4. For example, sensor 450 can be an electromagnetic time-of-flight sensor, thermopile sensor, thermal imaging camera, ultrasonic sensor, infrared sensor, etc.

In some implementations, sensing field 802 can be shaped as a cone. For example, the sensing field can have a particular width at the sensor 460 and extend in width in a direction away from the sensor 460. In some implementations, sensing field 802 can be shaped as a cylinder, rectangle, or other shape similarly as described above. In some implementations, the cone shape can be made wider or narrower. In some implementations, portions of the sensing field 802 (and/or sensing field 702 described for FIG. 7) can be blocked or adjusted in size or dimensions, e.g., by selecting particular settings of the sensors emitting the sensing fields, and/or physically masking portions of the sensor 460 to block portions of the standard sensing field of the sensor from being sensed. For example, this can prevent the sensor 460 from detecting objects such as grip members 406 or other components of handle 402 which are to be ignored.

In some implementations, a portion of handle 402 can extend into the sensing field 802, e.g., such that a portion of handle 402 intersects the sensing field. For example, a portion of a grip member 406 can extend into the sensing field 802 as shown in FIG. 8. For some types of sensors, reflected signals caused by such components of handle 402 can be sensed and normalized such that such handle components are ignored and new objects located within the sensing field are detected by the sensor 460.

The sensing field 802 in the configuration of FIG. 8 can be oriented such that a user's hand enters the sensing field as the hand approaches handle 402, e.g., to operate the handle. Thus, presence sensing system 430 can detect the presence of a hand before it has contacted handle 402 (including contacting grips 406 or central portion 407). In some implementations, the sensing system 430 can detect the hand before it contacts any part of the controller portion 400.

The configuration of the sensing field 802 effectively senses the presence of a hand operating handle 402. For example, while a hand grasps the two grip members 406, one or more portions of the hand extend into sensing field 802. This sensing field configuration can be used with a control input device of the system without changes needed for operation of handle 402 by a left hand or a right hand.

Each control input device of a control system can include its own presence sensing system of any of the implementations described herein, allowing each control input device to activate and deactivate a controlling mode independently of other controllers based on presence detection.

The sensing field(s) of described implementations are advantageous compared to contact sensors or sensors detecting presence on or very near a handle surface, since such sensors may not detect a hand in various operating conditions similarly as described.

Figure 9:
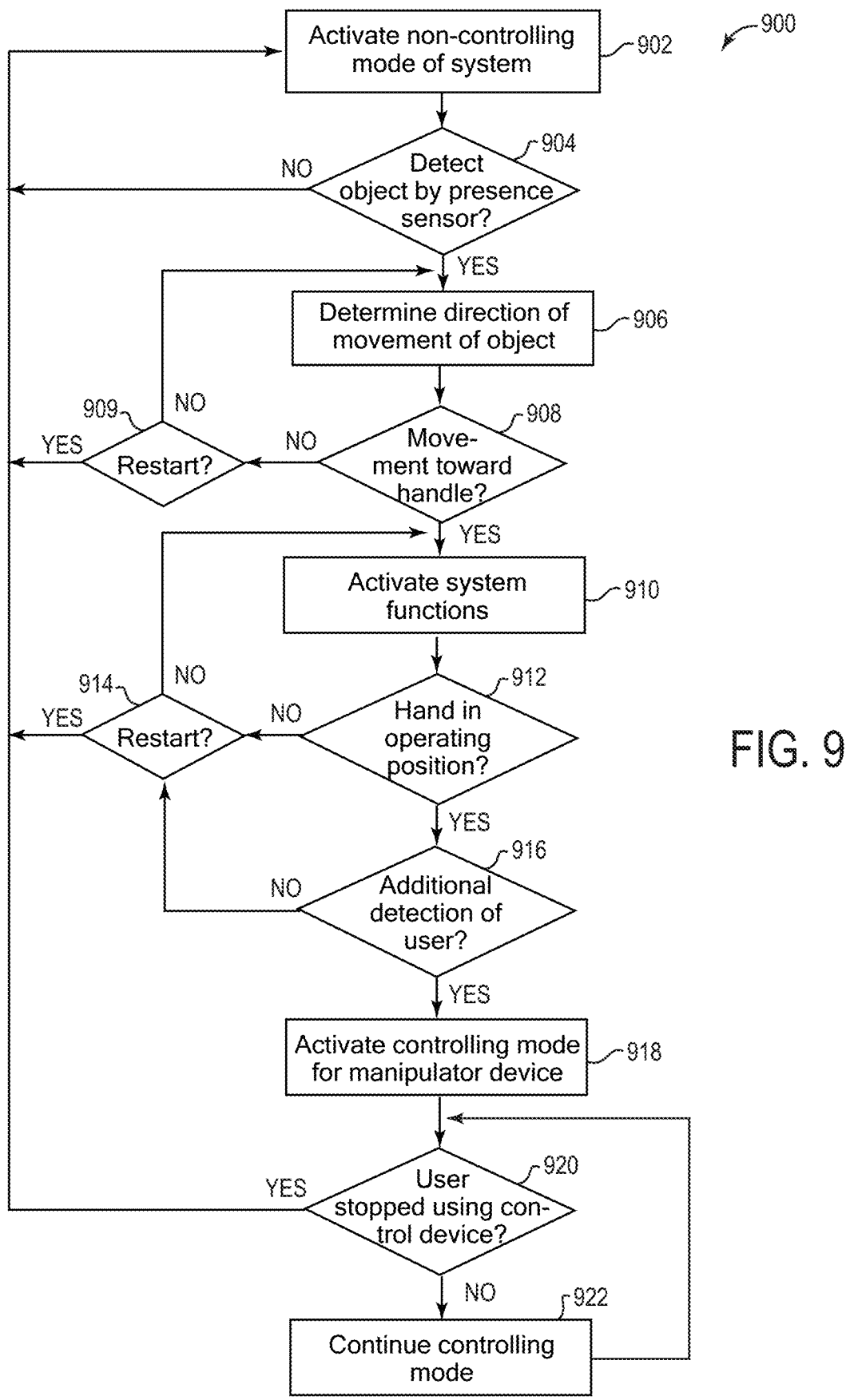
FIG. 9 is a flow diagram illustrating an example method to detect the presence of a user's hand to operate a control input device, according to some implementations.

FIG. 9 is a flow diagram illustrating an example method to detect the presence of a user's hand to operate a control input device, in some implementations. Method 900 can, for example, be performed by a control system, e.g., an example teleoperated system in which the control input device is included in a system that controls a manipulator device, e.g., manipulator system 104 of FIG. 1. In some implementations, the control input device is a component of a user control system, e.g., user control system 102 of FIG. 1. The control input device can be or include, for example, a portion 300 or 400 of control input device 210 or 212, or another control input device as described herein. In some implementations, the method can be performed by a controller circuit component coupled to the control input device. In some examples, the controller can include one or more processors, e.g., microprocessors or other control circuits, some examples of which are described below with reference to FIG. 11.

A single control input device is referred to in method 900 for explanatory purposes. Other implementations can use a control input device having one or more features described herein with other types of systems, e.g., non-teleoperated systems, a virtual environment (e.g., medical simulation) having no physical manipulator device and/or no physical subject interacting with a physical manipulator device, etc. Multiple control input devices can be similarly processed as described in method 900, e.g., both control input devices 210 and 212 of FIG. 2.

In block 902, a non-controlling mode of the control system (e.g., teleoperated system 100) is activated. The non-controlling mode can also be considered a "safe mode" in which the control input devices are not enabled to provide control signals to a controlled device such as manipulator system 104 if the control input devices are manipulated by the user. Thus, for example, the manipulator system is disconnected from the control input device for non-controlling mode, e.g., the manipulator system is not being controlled by the control input device. For example, the control input devices 210 and 212 can be manipulated by a user in non-controlling mode which will not cause any controlled motion of the elements of the manipulator system 104.

In block 904, it is determined whether an object is detected in the sensing field(s) of the hand presence sensing system of a control input device, e.g., presence sensing system 430 as described above. For example, the object may be an operator hand detected in the sensing field(s) of the hand presence sensing system of the control input device. Such detection can indicate that a user may be ready to start using the control input device, e.g., to control a manipulator device. The object may also be detected by other sensing systems of the system. In some implementations, the hand presence sensing system may be able to detect whether the object is a hand or is a different object, e.g., based on the magnitude of sensed temperature of the object being within a range of temperatures. In some of these cases, if the object is not detected as a hand, it can be ignored. In some implementations, a detected object within a sensing field of a hand presence sensor is considered to be a hand.

In some implementations, an object is considered to be detected by the hand presence sensing system (e.g., user hand presence detected so that block 918 is performed, below) if the object is detected to be within a particular sensing range, e.g., within a threshold distance to a reference location associated with the control input device. For example, the reference location can be location on a handle (e.g., handle 402) of the control input device, a location of one or more sensors of the hand presence sensing system, a surface of a finger grip, a defined point between two handle surfaces, etc. In some implementations, the hand presence sensing system may detect an object in its sensing field, but the object will be ignored for purposes of method 900 (e.g., cannot qualify as a hand presence detection) unless it is within the particular distance to the reference location.

If an object has not been detected, then the method can return to block 902 to continue the non-controlling mode of the control input device. If an object has been detected, then the method may continue to block 906, in which a direction of movement of the detected object can be determined (if appropriate). For example, if the presence sensing system 430 includes a time-of-flight sensor, thermal imaging camera, or other types of sensors as described above, then motion of the detected object can be tracked over time and the direction of movement determined from sensed data. In some implementations, the direction of the detected object can be indicated in a direction parameter used in the method, e.g., the direction parameter sent in signals to a control circuit. In some implementations, a velocity of the detected object can be determined as described above (which can include direction of movement and/or magnitude/speed of movement). In some implementations, the velocity can be used to determine whether to ignore the object for purposes of method 900 unless it meets a particular velocity threshold (e.g., has a velocity above, or alternatively below, the threshold). In some implementations, the velocity can be used to determine whether to use the position of the detected object (e.g., distance to control input device) in determining whether user presence is detected, similarly as described above. For example, fast velocity away from the control input device can indicate that object position is not needed, while slow velocity away from the control input device can indicate to examine object position to help determine user intent.

In some implementations, a timer can be used to provide a time limit for a continuous time period in which the control system is receptive to detecting a user's hand operating a control input device handle and activating controlling mode. For example, a timer can be started after an object is detected in block 904. Some implementations can start a timer based on other or additional conditions, or at other stages of the method 900.

In block 908, it is determined whether the detected movement of the object is in one or more first designated directions relative to the handle of the control input device. The first designated direction(s) are used to indicate potential user intent. For example, the designated direction can be toward the handle (or a reference location on the handle), such that the distance between object and handle decreases. Such a direction of movement can indicate that the user may be intending to move his or her hand to grasp the control input device. For example, a vector of the movement of the object can be estimated based on the obtained sensor data describing the last few positions of the object, and if this vector is within a threshold range of directions, then it is considered to be moving toward the handle. Other first designated directions can be used in some implementations, e.g., directions toward particular input controls of the handle, etc.

If the object is not determined to be moving in a designated direction relative to the handle (e.g., toward the handle), then the method can continue to block 909 in which it is determined whether to restart the detection process. For example, if a timer was started upon detection of an object after block 904 as described above, it is checked whether a timeout has occurred, e.g., a time period has expired, which indicates to restart the process. In some examples, the timeout period can be in a range 3 to 10 seconds. In some implementations, if it is determined that the direction of the object is a second designated direction that indicates user intent not to immediately use the handle, the detection process can be restarted. For example, the second designated direction can be away from the handle in a particular threshold range of directions (e.g., moving in a direction that is away from a reference location on the handle such that it increases the distance therebetween). In some implementations, the direction of the object can be determined based on detecting a distance from a sensor to the object over time, e.g., with multiple measurements. In some implementations, a determined velocity of the detected object can be used to assist determination of user intent to immediately use the handle, e.g., if it has a velocity above a velocity threshold.

In some implementations, if the object leaves the sensing field(s) of the presence sensing system, the detection process can be restarted. If it is determined to restart the detection process, the method returns to block 902. Otherwise, the method returns to block 906 to continue to determine the direction of the object, e.g., to determine if its movement changes direction toward the handle.

If the object is determined to be moving toward the handle in block 908, then the method continues to block 910, in which one or more system functions are activated. For example, one or more graphical user interfaces (GUIs) of the control system may have been turned off and not displayed on display devices of the system (e.g., display screens, augmented reality displays, virtual reality displays, etc.) during the non-controlling mode. Such displays can be activated in block 910 such that display objects or features of the GUIs are displayed. In some implementations, features or objects of the GUIs may have been in a dimmed state in the non-controlling mode, and are brightened in block 910 from the prior dimmed state. In some implementations, activated functions can include supplying power to one or more components of the system, such as motors of the control input device to provide force feedback and/or gravity compensation, motors of a manipulator device that are configured to move arms and/or instruments, cameras for viewing a operating site, lights for illuminating instruments and/or operating site, manipulator instrument functions (e.g., suction, irrigation, energy, etc.), etc. In some implementations, activated functions can include moving the handle to a particular starting position in the workspace of the control input device, e.g., via control of motors on connected linkages. In some example implementations, activated functions can include moving all or part of other components of the control system to starting positions via control of motors. Such components can include display devices (e.g., screens, viewers, etc.), foot pedals, seats, etc. The method continues to block 912.

In block 912, it is determined whether the object (e.g., a hand of the user) has been detected in an operating position of the control input device (e.g., an "operating detection"). For example, the hand presence sensing system can detect whether the user's fingers and/or palm are in a position, or sufficiently close to a position, that allows the hand to operate the control input device in the intended manner. In some implementations, it is detected whether the hand is at a particular position, such as within a threshold distance of a particular reference location (e.g., a location on a surface of the handle or adjacent to a surface of the handle, such as a surface of a grip member 406, or a location of a sensor of the presence sensing system). As in the examples of FIGS. 4-8, the hand presence sensing system can detect whether the detected portion of the hand is at or near a particular location within the sensing field(s) of the sensing system, e.g., palm portion of the hand in a position in front of the distal end 405, fingers positioned against the grip members 406, etc. In some implementations, the hand is considered to be in an operating position if a threshold amount or percentage of the sensed field is occupied by a hand, or in some implementations, if one or more particular locations within the sensed field are occupied by the hand. In some implementations, the hand is considered to be in an operating in an operating position if it is detected anywhere within the sensing field(s) of the hand presence sensing system, e.g., near the handle, contacting the handle, etc. In some implementations, if a particular distance is checked in block 904 as described above, the threshold distance of block 912 can be different (e.g., smaller, thus detecting the hand closer to the handle) than the particular distance of block 904. In some implementations, multiple sensing fields of multiple individual sensors on the control input device can be used to determine whether object detection has occurred, e.g., as described above with respect to FIG. 4.

If the hand is not detected in an operating position, the method continues to block 914 in which it is determined whether the detection process should be restarted, similarly as described above for block 909. For example, it is determined whether a timeout has occurred, or if the detected object is moving away from the handle. If the detection process is to be restarted, then the method returns to block 902 to continue non-controlling mode. Otherwise, the method returns to block 910 to continue to activate system functions.

If the hand is detected in an operating position in block 912, then the method may continue to block 916 in which it is determined whether there has been additional detection by the system of the presence of the user in an operating position of the control input device and/or control system. For example, the presence sensor 214 described above with reference to FIG. 2 can detect the presence of a user's head in a viewing recess 211 of user control system 102, indicating intended use of the control input devices 210 and 212 by the user. In some implementations, the user is required to move the grip members 406 to a particular position in the grip members' degree of freedom, e.g., to match a position or orientation of a manipulator instrument to be controlled by the control input device (and provides other safety features). In some implementations, other or additional presence sensors can be used to sense user presence. Such additional presence detection acts as an additional check or safeguard in detecting a user before activating controlling mode. In some implementations, if such additional sensing is utilized, one or more thresholds used by the system to detect a user and activate controlling mode can be reduced to allow presence requirements to be more easily satisfied. For example, thresholds of object detection used by the presence sensing system 430 and/or presence sensor 214 can be eased (e.g., magnitude of sensed signal, time for detection to be verified, etc.), allowing quicker confirmation of user presence. Some implementations can omit block 916.

If there is no additional detection of the user as determined in block 916, the method continues to block 914 to check for a restart to the detection process as described above. If additional detection of the user is determined in block 916 (or additional detection is not implemented), the method continues to block 918.

In block 918, a controlling mode of the system is activated. Controlling mode allows the manipulations of the control input device to control functions of a controlled manipulator device. For example, in a teleoperated system, the manipulations of the control input device can control corresponding motions, output functions (output of heat, electricity, etc.), and/or other functions of a manipulator device in controlling mode, such as moving an end effector in space, opening jaws of the end effector, outputting heat or other energy from the end effector, etc. In some implementations, controlling mode can be activated for a corresponding component of the manipulator device that is controlled by the control input device.

In some implementations, feedback output from one or more components of the system can indicate to the user that controlling mode is active and that the control input device now controls a manipulator device, e.g., the manipulator system 104. In some implementations, the output can include visual output from display devices, audio output from audio devices, forces output on the control input device from motors, etc. The method continues to block 920.

In block 920, it is determined whether the user has stopped operating the control input device. This determination can be made in multiple ways in various implementations. In some implementations, a change in the presence of the hand is detected by the presence sensing system 430, and the system considers this change to indicate that the user has stopped operating the control input device. In some examples, the indication that the user is ceasing operation of the control input device can include a release of the user's touch or grip of the hand on the handle of the control input device. The user's release of touch or grip on the handle can be detected by the system based on the sensor signals from the hand presence sensing system 430.

In some example implementations, the indication of ceasing operation can be the hand (or a portion of the hand) moving out of the sensing field(s) of the presence sensing system such that the presence sensing system 430 no longer detects the hand (or the portion of the hand). In another example, the indication can be detecting the hand (or portion thereof) in a location outside of a threshold distance or radius from a reference location of the control input device (e.g., a reference location such as a location on the handle or a sensor of the hand presence sensing system). In another example, the indication can be detecting movement of the hand of the user in a particular direction relative to the handle or a reference location of the control input device, e.g., in a direction away from the handle or away from a reference location (e.g., within a threshold range of vector directions away from a reference location on the handle). A combination of these indications and/or other indications can be used as a determination that the user has stopped operating the control input device.

Furthermore, other presence sensors (or other types of sensors) of the system can be used to detect a user stopping operation. For example, the presence sensor 214 of FIG. 2 can sense whether the head of the user has been removed from the viewing position. In some implementations, if any presence sensor of the system no longer detects the presence of the user, the user is determined to have stopped operating the control input device. In some implementations, actions of a manipulator device (e.g., removal of a surgical instrument from a defined operating area or worksite) may be used to indicate that the user has stopped operation.

If cessation of user operation of the control input device is not detected, then the method continues to block 922 to continue providing the controlling mode of the control system, and the method returns to block 920 to continue checking for an indication that the user has stopped operating the control input device. If, in block 920, it is detected that the user has stopped operating the control input device, then the method returns to block 902 to activate the non-controlling mode of the system. For example, control of the manipulator device 104 is disconnected from the control input device based on the detection that the user is no longer operating the control input device. At block 902 and following blocks, the method can check for a user operating the control input device as described above.

In some implementations, the system can enter additional or alternate states upon detecting that the user has stopped operating the control input device (e.g., at block 920). For example, upon loss of detection of the user's hand, a hold or pause of the controlling mode can be made active, such that, if the hand is again detected within a threshold period of time, the controlling mode can be re-entered more easily (e.g., with lower thresholds as described above) than when restarting the detection process from block 902. In some implementations, upon loss of detection of the user's hand, a power save mode of the system can be entered, and the power save mode can be exited when the hand is again detected.

In various implementations, a time delay can be provided after a qualifying detection is made that causes the system to activate controlling mode and/or to activate non-controlling mode. For example, the time delay delays the activation of the controlling mode and/or non-controlling mode. In some examples, upon determining in block 916 that controlling mode should be activated (e.g., upon detection of hand presence and other user presence), the system waits for a delay of 1 second (or 2 seconds, etc.) before controlling mode is made active. A similar delay can be provided after determining to activate non-controlling mode, such that the activation of the non-controlling mode is delayed.

In some implementations, upon loss of detection of a user's hand at block 920, the process may return to block 910 to activate (and/or deactivate) one or more system functions, e.g., particular input controls, settings, and/or inputs of the system can be made active. Examples of such system functions can include input devices on an armrest of a user control system (e.g., an armrest touchscreen on armrest 110) becoming active and receptive to user input, or a handle or switch to control a position of a viewing device or display device to become active and receptive to user input. In some implementations, these functions and other functions that are not used during manipulation of the control input device can be disallowed or deactivated (e.g., input to control these functions can be ignored) during detection of user hand presence at the control input device, e.g., at block 920. If the user's hand presence is no longer detected, then these functions can be made active. In some implementations, the particular hand(s) having presence detected can be utilized to determine which controls are activated. For example, if only the user's left hand is removed from a control input device so that the presence of the hand is no longer detected, then particular input controls and/or functions that are accessible to the left hand are made active, but input controls and/or functions accessible to only the right hand are not made active, since the presence of the right hand is still detected at a different control input device.

In some implementations, multiple control input devices may be used, e.g., each control device is simultaneously manipulated by a respective hand of a user. In one example, multiple control input devices 210 and 212 can be used as shown in FIG. 2. In some of these implementations, each of the control input devices has a range of motion such that a first control input device may be positioned within the sensing field (e.g., as described herein) of the presence sensing system of a second control input device. In some implementations, this positioning may cause a false positive detection of the first control input device by the presence sensing system of the second control input device, e.g., a mistaken detection of the presence of a user hand operating the second control input device. To reduce the occurrence of such false positive detections, the position and/or orientations of each control input device in its workspace can be tracked by a control block coupled to the control input devices (e.g., control block 1110 of FIG. 11). For example, device sensors that detect the positions of the control input devices (e.g., sensors that detect relative positions or orientations of links of a kinematic chain) can be used to determine these positions and orientations of control input devices.

In some of these implementations, if a detection of an object is performed in method 900 (e.g., in block 904 and/or block 912), then the system checks the current position(s) and/or orientation(s) of the other control input device(s) to determine whether the detected object is a control input device that has been sensed by the presence sensing system. If it is determined that a control input device has been sensed, then the detection of the object is ignored, e.g., treated as if no object has been detected. If it is determined that a control input device has not been sensed, then the system examines the detected object as described above for method 900. In some implementations, signals from other sensors (such as head presence sensor 214) can be examined as another factor to indicate whether to ignore the detected object. For example, if the user's head is detected by sensor 214, then the detection of the object may be acknowledged and not ignored.

In some other implementations, if a control input device is determined to be the detected object as described above, the detection of the object is acknowledged and not ignored, but one or more other parameters or thresholds that are used to cause controlling mode to be activated in block 918 can be made tighter or more strict, thus providing stricter conditions (and more certain detection) to detect user presence. For example, other presence sensors (e.g., head presence sensor 214) can be assigned a closer threshold distance or smaller sensing field to determine detection of user presence. In another example, grip members 406 can be required to be positioned in a smaller range of positions to match a position or orientation of a controlled manipulator instrument, in order to allow controlling mode to be active. Other examples of setting or adjusting detection parameters or other presence system features based on presence detection are described below with respect to FIG. 10.

Various implementations can use different portions of the methods disclosed herein. For example, some implementations can perform blocks 902, 904, 910, 918, 920, and 922 without other blocks; some implementations can perform blocks 902, 904, 910, 912, 918, 920, and 922 without other blocks; some implementations can perform one or more blocks without block 904; etc.

The blocks described in the methods disclosed herein can be performed in a different order than shown and/or simultaneously (partially or completely) with other blocks, where appropriate. Some blocks can be performed for one portion of data and later performed again, e.g., for another portion of data. Not all of the described blocks need be performed in various implementations. In some implementations, blocks can be performed multiple times, in a different order, and/or at different times in the methods. For example, blocks 904, 908, 912, and/or 916 can be performed sequentially, at least partially at the same time, or in a different order.

In another example implementation, a method includes activating a controlling mode in response to detecting the hand presence of the user, and activating a non-controlling mode in response to detecting absence of hand presence of the user. In some implementations, the controlling mode is activated only in response to both detecting the hand presence of the user and detecting presence of the user by one or more other presence detection devices of the control system that includes the control input device. For example, the other presence detection devices can include a head presence sensor (e.g., as shown in FIG. 2), one or more grips of the control input device that have been moved to a particular position, etc.

Figure 10:
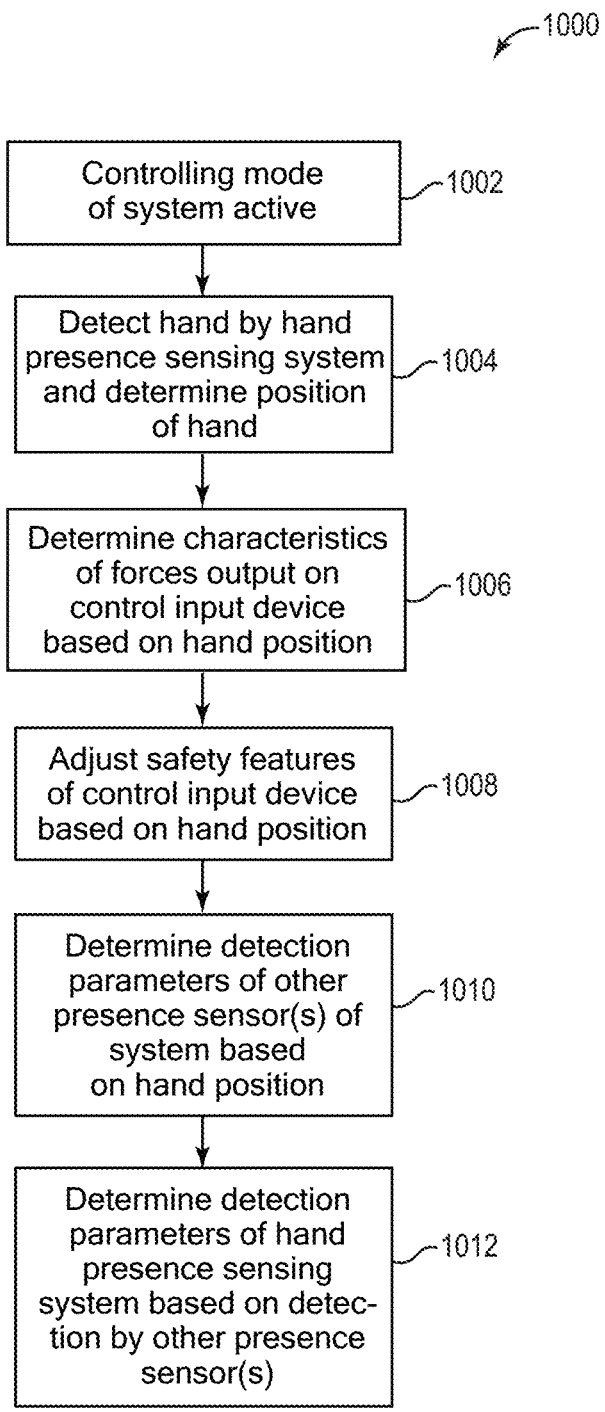
FIG. 10 is a flow diagram illustrating an example method to determine and/or adjust presence sensing features and/or other system features based on presence sensor data, according to some implementations.

FIG. 10 is a flow diagram illustrating an example method 1000 to determine and/or adjust presence sensing features and/or other system features based on presence sensor data, according to some implementations. In some implementations, method 1000 can be performed in a system that also performs method 900 of FIG. 9, or alternatively, method 1000 (or various blocks or portions of method 1000) can be performed with other methods or systems having suitable presence sensing.

Method 1000 can, for example, be performed for a control system, e.g., an example teleoperated system or other control system in which the control input device is included in a system that controls a manipulator device. In some implementations, the control input device is a component of a user control system, e.g., user control system 102 of FIG. 1. The control input device can be, for example, a portion 300 or 400 of control input device 210 or 212, or another control input device as described herein. In some implementations, method 1000 can be performed by a circuit component coupled to the control input device. In some examples, the controller can include one or more processors, e.g., microprocessors or other control circuits, some examples of which are described below with reference to FIG. 11. A single control input device is referred to in method 1000 for explanatory purposes. Other implementations can use a control input device having one or more features described herein with other types of systems, e.g., non-teleoperated systems, a virtual environment (e.g., medical simulation) having no physical manipulator device and/or no physical subject interacting with a physical manipulator device, etc. Multiple control input devices can be similarly processed as described in method 1000, e.g., both control input devices 210 and 212 of FIG. 2.

In block 1002, a controlling mode of the control system (e.g., teleoperated system 100) is active. The controlling mode can be similar as described with reference to FIGS. 9 and 11, e.g., a mode in which the control input devices are enabled to provide control signals to a controlled device such as manipulator system 104 as the control input devices are manipulated by the user. For example, the control input devices 210 and 212 can be manipulated by a user while controlling mode is active, which causes corresponding motion of elements of the manipulator system 104 and/or changes of other functions of the manipulator system 104.

In block 1004, a hand is detected by the hand presence sensing system and a position of the hand is determined. For example, the position can be a distance of the hand relative to a reference location of the control input device as determined as described herein. In some examples, the hand can be detected in one or more sensing fields as described in various implementations herein, e.g., within a threshold distance of a reference location of the control input device, and/or satisfying other conditions to be considered a hand detection that allows controlling mode to be activated as described herein. The distance of the hand can be determined as a distance between the hand (or a portion thereof) and the reference location, which can be an end of a handle, sensor, finger grip, or other location, etc. The distance or other position can be determined as described herein for any of various sensor types and implementations. In some implementations, movement and a direction of the movement of the hand can also be determined in block 1004 similarly as described above.

In block 1006, characteristics of forces output on the control input device can be determined based on the hand position determined in block 1004 and forces with such characteristics are output as appropriate. The output forces include forces output in one or more degrees of freedom of the control input device by one or more actuators, e.g., motors. For example, the determined force characteristics can include a maximum force (force limit) on the control input device. In some implementations, if the hand is detected more than a threshold distance away from the reference location of the control input device, the maximum force can be set to a smaller magnitude than if the hand is detected at a distance closer than the threshold distance. In some examples, this threshold distance can be independent of (e.g., smaller than) the presence sensing threshold distance described above. In some examples, the maximum force can be gradually adjusted to any of multiple magnitudes based on different distances of a detected hand, or can be set at one of two possible magnitudes based on the threshold distance, etc. In some implementations, if the hand is detected to be at longer distances of the hand presence sensing range, it is more uncertain whether the user is intending to continue operating the control input device compared to hand locations at distances closer to the control input device. Therefore, the forces on the control input device are reduced for safety, e.g., so that the control input device is not moved as much by the forces away from the user if the user is detected to be using the control input device by the hand presence sensing system but the user is not grasping the control input device.

In additional examples, the determined force characteristics can include magnitudes or gain of the output forces based on the hand position determined in block 1004. For example, all of the forces output on the control input device can be reduced in magnitude by a particular percentage that is based on the sensed distance of the hand (or distance of the hand that is greater than a particular distance threshold). A force ramping rate can be similarly based on the hand distance determined in block 1004, e.g., a rate at which forces are increased to a particular magnitude. Any one or more of the described force characteristics can be determined and used in block 1006 in various implementations.

In block 1008, safety features of the control input device are adjusted based on the hand position determined in block 1004. Some examples of safety features include techniques to detect particular patterns (e.g., sequences) of motion, acceleration, changes in direction, etc. of the control input device in one or more of its degrees of freedom. The patterns can indicate whether the user is actively controlling or not actively controlling the control input device (e.g., a control input device moving or "floating" on its own would not match the pattern, would not move in particular degrees of freedom, etc.). The adjustment of such safety features in block 1008 can include, for example, changing the parameters (e.g., thresholds or limits) of the techniques based on the detected position (e.g., distance) of the hand. For example, if the hand is sensed at longer distances (e.g., greater than a threshold distance), parameters can be changed to require detection of shorter movements, higher accelerations, and/or more or greater changes in direction of the control input device in order to detect active user control of the control input device that would continue activation of the controlling mode, as compared to shorter sensed distances of the hand (e.g., below the threshold distance). This reflects the uncertainty of user intent at longer sensed distances of the hand, such that increased safety measures are provided.

Another example of a safety feature includes a limit for the velocity of the control input device in one or more degrees of freedom. For example, the velocity can be physically reduced by controlling one or more force output devices (e.g., brakes, motors, etc.) that are coupled to the control input device, to apply forces to slow the maximum allowed velocity of the control input device in associated degrees of freedom. In some examples, a control system can monitor the velocity of the control input device and can command output motor torque that is proportional to the velocity of the control input device to slow the motion of the control input device when the velocity is above a threshold. The controller and motor thus can provide damping to the control input device to slow it down. For example, if the hand is sensed at longer distances (e.g., more than a threshold distance), the maximum velocity can be lowered in comparison to shorter sensed distances of the hand (e.g., below the threshold distance). Some implementations can use a sensed direction and/or velocity of the hand in the determination of safety feature adjustment, e.g., based on whether the direction is toward or away from the control input device.

In block 1010, one or more detection parameters of other presence sensor(s) of the control system (e.g., a control console of a teleoperated system) are determined based on the hand position determined in block 1004. The other presence sensors are independent and separate from the hand presence sensing system that senses the presence of a user's hand as described herein. Other presence sensors can include, for example, the head presence sensor 214 of FIG. 2 that detects a head of a user, and/or other presence sensors (e.g., a body detection sensor, foot detection sensor, etc.). Determining detection parameters of such other presence sensors can include, for example, determining one or more thresholds of sensing, ranges of sensing, and/or durations of sensing.

For example, if the hand presence sensing system detects a position of a hand, e.g., in a particular range (e.g., more than a threshold distance from the control input device), tighter or stricter range(s) and/or threshold(s) of detection can be set for the head presence sensor 214 as compared to when shorter distances are sensed for the hand (e.g., outside the particular range or below the threshold distance). The tighter ranges and/or thresholds cause the head presence sensor to detect user presence via the user's head under stricter conditions (e.g., with less tolerance), e.g., when the head is closer to or within a more precise location relative to the head presence sensor, and/or is sensed for a longer duration (period of time), as compared to sensing with looser ranges and/or thresholds. This can allow the other presence sensors to provide more certain user detection, e.g., to compensate when the hand presence sensing system may have detected user presence with less certainty, e.g., when the user's hand is further from the control input device and/or appears likely to disconnect from the control input device. Multiple distance thresholds for the hand sensing can be used in some implementations, e.g., to set various associated values of the detection parameters of the other presence sensor(s) based on the hand's detected position relative to the thresholds.

In block 1012, one or more detection parameters of the hand presence sensing system are determined based on detection by other presence sensor(s) of the control system (e.g., a user control system 102 of a teleoperated system 100). As in block 1010, the other presence sensor(s) can include, for example, the head presence sensor 214 of FIG. 2 and/or other presence sensors. For example, it can be determined whether another presence sensor has detected the user within one or more thresholds defining a particular presence range. In some examples, the particular presence range can be close to bounds of the other presence sensor, e.g., detection within a particular distance range of a limit of a sensed range, or within a particular distance range to a threshold indicating detection. For example, the user's head may be detected within a particular presence range that is at the limit of a range of locations qualifying for presence detection. In some implementations, the particular presence range can be specified as a distance range or position range defined by thresholds.

In response to user detection within the particular presence range of the other presence sensor(s), one or more detection parameters are set or adjusted for the hand presence sensing system. Such detection parameters of the hand presence system can include, for example, the bounds of sensing, e.g., a threshold, range, direction, velocity, and/or a duration of sensing. In some examples, if a sensed position of the user's head is in the particular presence range, e.g., more than a threshold distance from a reference location of the head presence sensor, one or more tighter/stricter ranges and/or thresholds of sensing can be set for the hand presence sensing system compared to when sensed positions of the head are outside the presence range, e.g., below the threshold distance from the reference location of the head presence sensor.

The tighter ranges and/or thresholds of sensing cause the hand presence sensing system to detect user presence via the user's hand under stricter conditions (e.g., with less tolerance). For example, the stricter conditions can include the hand being closer to the control input device, moving in a direction more directly toward the control input device, having a lower velocity (e.g., in a particular direction), and/or being sensed for a longer duration (period of time), as compared to sensing with looser ranges and/or thresholds when the user's head (or other sensed user presence) is detected outside the particular presence range. For example, this allows the hand presence sensing system to provide more certain user detection when other presence detectors may have detected user presence with less certainty. Multiple thresholds for the other presence sensors can be used in some implementations, e.g., to set various values of the detection parameters of the hand presence sensing system based on user presence detected relative to the thresholds.

In some implementations, any one or more of the above blocks 1006, 1008, 1010, and/or 1012 can use alternative or additional characteristics of a detected object to determine the presence sensing features described in these blocks. For example, a determined direction of movement of the detected hand, and/or a determined velocity of the hand, can be used in the determination of output forces in block 1006 (e.g., by reducing output force magnitudes if the direction is away from the control input device), safety features of block 1008, and presence detection parameters of block 1010 and/or 1012. In various implementations, a sensed pose of a hand (e.g., sensed orientation and position of the hand in space) can be used in the determination of the presence sensing features in any of the blocks 1006, 1008, 1010, and/or 1012; for example, particular poses can be associated with particular forces or detection parameters determined in blocks 1006, 1008, 1010, and/or 1012.

Various implementations can use different portions of the methods disclosed herein. For example, various implementations can perform any one or more blocks of the set of blocks 1006, 1008, 1010, or 1012 without performing one or more other blocks of this set. In some examples, one implementation can perform only blocks 1002, 1004, and 1006; another implementation can perform only blocks 1002, 1004, and 1008; another implementation can perform blocks only 1002, 1004, and 1010; and another implementation can perform only blocks 1002, 1004, and 1012.

The blocks described in the methods disclosed herein can be performed in a different order than shown and/or simultaneously (partially or completely) with other blocks, where appropriate. Some blocks can be performed for one portion of data and later performed again, e.g., for another portion of data. Not all of the described blocks need be performed in various implementations. In some implementations, blocks can be performed multiple times, in a different order, and/or at different times in the methods.

Figure 11:
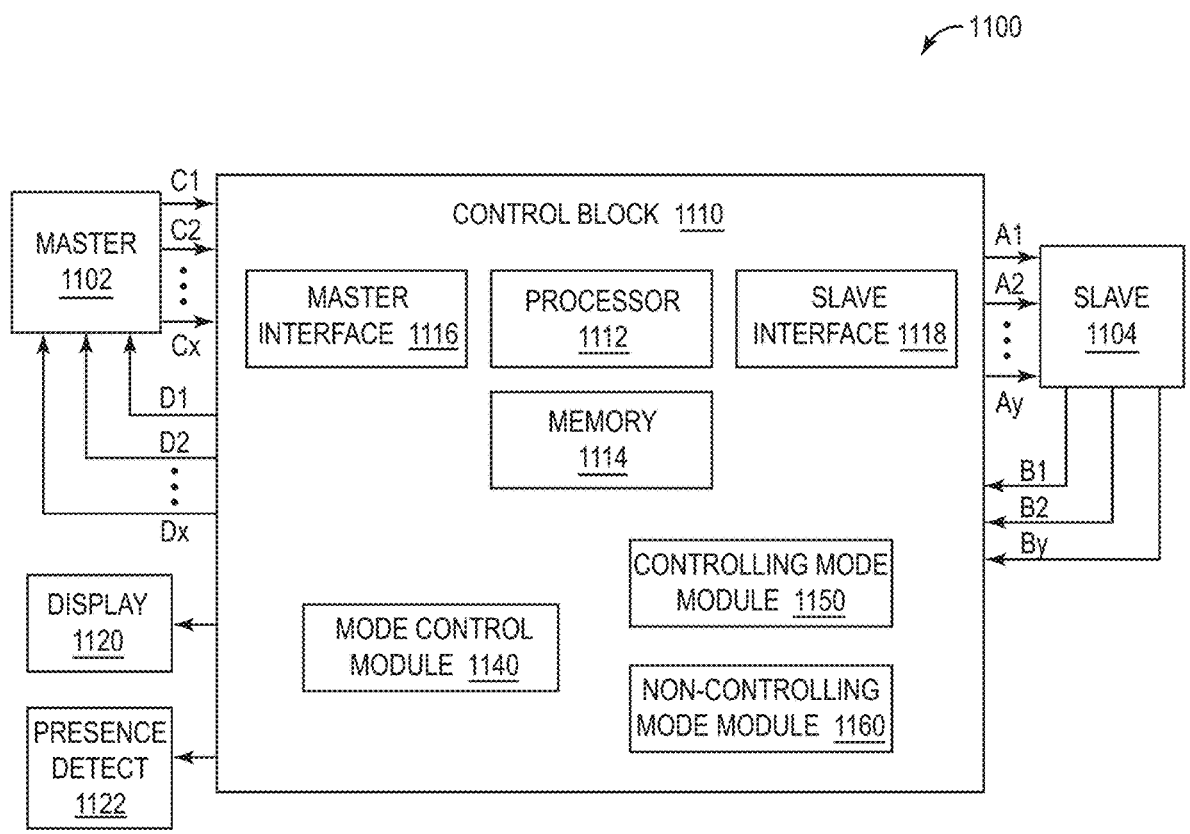
FIG. 11 is a block diagram of an example control system which can be used in one or more implementations described herein.

FIG. 11 is a block diagram of an example control system 1100 which can be used with one or more features described herein. System 1100 includes a master device 1102 that a user may manipulate in order to control a slave device 1104 in communication with the master device 1102. In some implementations, master device 1102 can be, or can be included in, user control system 102 of FIG. 1. In some implementations, slave device 1104 can be, or can be included in, manipulator system 104 of FIG. 1. More generally, master device 1102 can be any type of device including a control input device (e.g., including portion 300 or 400 of a control input device) that can be physically manipulated by a user. Master device 1102 generates control signals C1 to Cx indicating positions, states, and/or changes of one or more control input devices in their degrees of freedom. The master device 1102 can also generate control signals (not shown) to control block 1110 indicating selection of physical buttons and other manipulations by the user. The master device 1102 can also generate control signals to control block 1110 including detection data associated with detection of user presence by one or more user presence sensing systems, e.g., a head presence sensing system and/or a hand presence sensing system of the master device 1102 as described herein (e.g., indication of hand detection, detection parameters including distance, direction, and/or velocity of detected objects, etc).

A control block 1110 can be included in the master device 1102, in the slave device 1104, or in a separate device, e.g., an intermediary device between master device 1102 and slave device 1104. In some implementations, the control block 1110 can be distributed among multiple of these devices. Control block 1110 receives control signals C1 to Cx and generates actuation signals A1 to Ay, which are sent to slave device 1104. Control block 1110 can also receive sensor signals B1 to By from the slave device 1104 that indicate positions, orientations, states, and/or changes of various slave components (e.g., manipulator arm elements). Control block 1110 can include general components such as a processor 1112, memory 1114, and interface hardware 1116 and 1118 for communication with master device 1102 and slave device 1104, respectively. Processor 1112 can execute program code and control basic operations of the system 1100, including functions related to sensing the switch mechanisms described herein, and can include one or more processors of various types, including microprocessors, application specific integrated circuits (ASICs), and other electronic circuits. Memory 1114 can store instructions for execution by the processor and can include any suitable processor-readable storage medium, e.g., random access memory (RAM), read-only memory (ROM), Electrical Erasable Read-only Memory (EEPROM), Flash memory, etc. Various other input and output devices can also be coupled to the control block 1110, e.g., display(s) 1120 such as the viewer 213 of the user control system 102 and/or display 124 of FIG. 2. One or more other presence sensors 1122 can provide signals to control block 1110 indicating detection of user presence and/or parameters related to such detection, e.g., head presence sensor 214 of FIG. 2 and hand presence sensor systems described herein.

In this example, control block 1110 includes a mode control module 1140, a controlling mode module 1150, and a non-controlling mode module 1160. Other implementations can use other modules, e.g., a force output control module, sensor input signal module, etc. In some implementations, the modules 1140, 1150, and 1160 can be implemented using the processor 1112 and memory 1114, e.g., program instructions stored in memory 1114 and/or other memory or storage devices connected to control block 1110.

Mode control module 1140 can detect when a user initiates a controlling mode and a non-controlling mode of the system, e.g., by user selection of controls, sensing a presence of a user at a user control system or control input device, sensing required manipulation of a control input device, etc. The mode control module can set the controlling mode or a non-controlling mode of the control block 1110 based on one or more control signals C1 to Cx.

In some implementations, controlling mode module 1150 may be used to control a controlling mode of control block 1110. Controlling mode module 1150 can receive control signals C1 to Cx and can generate actuation signals A1 to Ay that control actuators of the slave device 1104 and cause it to follow the movement of master device 1102, e.g., so that the movements of slave device 1104 correspond to a mapping of the movements of master device 1102. Controlling mode module 1150 can also be used to control forces on the control input device of the master device 1102, e.g., forces output on one or more components of the control input device, e.g., grip members, using one or more control signals D1 to Dx output to actuator(s) used to apply forces to the components, e.g., to the grip members of the control input device, in a rotary degree of freedom of the control input device, on arm links coupled to the control input device, etc. In some examples, control signals D1 to Dx can be used to provide force feedback, gravity compensation, etc.

In some implementations, a non-controlling mode module 1160 may be used to control a non-controlling mode of system 1100. In the non-controlling mode, movement in one or more degrees of freedom of master device 1102, or other manipulations of master device 1102, has no effect on the movement of one or more components of slave device 1104. In some implementations, non-controlling mode can include one or more other operating modes of the control block 1110, e.g., a selection mode in which movement of the control input device in one or more of its degrees of freedom and/or selection of the control switches of the control input device can control selection of displayed options, e.g., in a graphical user interface displayed by display 1120 and/or other display device. A viewing mode can allow movement of the control input device to control a display provided from cameras, or movement of cameras, that may not be included in the slave device 1104. Control signals C1 to Cx can be used by the non-controlling mode module 1160 to control such elements (e.g., cursor, views, etc.) and control signals D1 to Dx can be determined by the non-controlling mode module to cause output of forces on the control input device during such non-controlling modes, e.g., to indicate to the user interactions or events occurring during such modes.

Some implementations described herein, e.g., methods 900 and/or 1000, can be implemented, at least in part, by computer program instructions or code which can be executed on a computer. For example, the code can be implemented by one or more digital processors (e.g., microprocessors or other processing circuitry). Instructions can be stored on a computer program product including a non-transitory computer readable medium (e.g., storage medium), where the computer readable medium can include a magnetic, optical, electromagnetic, or semiconductor storage medium including semiconductor or solid state memory, magnetic tape, a removable computer diskette, a random access memory (RAM), a read-only memory (ROM), flash memory, a rigid magnetic disk, an optical disk, a memory card, a solid-state memory drive, etc. The media may be or be included in a server or other device connected to a network such as the Internet that provides for the downloading of data and executable instructions. Alternatively, implementations can be in hardware (logic gates, etc.), or in a combination of hardware and software. Example hardware can be programmable processors (e.g. Field-Programmable Gate Array (FPGA), Complex Programmable Logic Device), general purpose processors, graphics processors, Application Specific Integrated Circuits (ASICs), and the like.

The functional blocks, operations, features, methods, devices, and systems described in the present disclosure may be integrated or divided into different combinations of systems, devices, and functional blocks.

Although the present implementations have been described in accordance with the examples shown, there can be variations to the implementations and those variations are within the spirit and scope of the present disclosure. Accordingly, many modifications may be made without departing from the spirit and scope of the appended claims.

What is claimed is:

1. A control input device comprising:
   a base member;
   a handle coupled to the base member and configured to be manually contacted at a grip portion of the handle and moved by a hand of a user in one or more degrees of freedom;
   one or more control input sensors configured to detect positions or orientations of the handle in the one or more degrees of freedom; and
   a presence sensing system coupled to the base member, the presence sensing system including a presence sensor having a sensing field, and at least a portion of the sensing field being located proximate to the handle, wherein a signal generated by the presence sensing system comprises a parameter, the parameter comprising a value that indicates:
      a direction of motion of the hand in the sensing field relative to the presence sensor, or
      a velocity of the hand in the sensing field, wherein the velocity includes the direction of motion of the hand in the sensing field relative to the presence sensor.

2. The control input device of claim 1, wherein the presence sensor is configured to detect electromagnetic radiation or an ultrasonic wave that is directed through space to the presence sensor by a presence of the hand in the sensing field of the presence sensor.

3. The control input device of claim 1, wherein the sensing field is shaped as, or approximately as, a cone that increases in width in a direction away from the presence sensor.

4. The control input device of claim 1, wherein:
   the handle includes a central member, wherein a central axis is defined between a distal end and a proximal end of the central member;
   the presence sensor is a first presence sensor configured to detect first electromagnetic radiation, and the sensing field is a first sensing field located at a first side of the handle;
   the presence sensing system further comprises a second presence sensor coupled to the base member;
   the second presence sensor is configured to detect second electromagnetic radiation that is directed through space to the second presence sensor by a presence of the hand in a second sensing field of the second presence sensor; and
   the second sensing field is proximate to the handle and is located at a second side of the handle that on an opposite side of the central member to the first side.

5. The control input device of claim 1, wherein:
   the parameter also indicates a variable distance between an object in the sensing field and the presence sensor.

6. The control input device of claim 1, wherein:
   the presence sensor includes an electromagnetic sensor;
   the presence sensor includes and emitter and a detector;
   the emitter is configured to emit a first electromagnetic signal in the sensing field; and
   the detector is configured to detect the first electromagnetic signal reflected from the hand in the sensing field.

7. The control input device of claim 1, wherein the value indicates the direction of motion of the hand based on multiple positions of the hand detected by the presence sensor in the sensing field over time.

8. The control input device of claim 1, wherein:
   the presence sensor includes a thermopile sensor or a thermal imaging camera; and
   the thermopile sensor or the thermal imaging camera includes a detector configured to detect infrared radiation emitted by the hand in the sensing field.

9. The control input device of claim 1, wherein:
   a central portion of the handle includes a handle distal end, a handle proximal end opposite the handle distal end, and a central axis defined between the handle distal end and the handle proximal end;
   the handle distal end is closer than the handle proximal end to the hand;
   a base portion of the base member includes a base distal end and a base proximal end opposite the base distal end;
   the base portion extends parallel or approximately parallel to, and offset from, the central axis and the central portion of the handle; and
   the presence sensor is located on the base distal end that is closer than the base proximal end to the handle distal end.

10. The control input device of claim 1, wherein:
    the handle includes a central portion that extends along a central axis of the handle between a distal end and a proximal end of the handle;
    the handle includes two grip members extending from the central portion;
    the two grip members are each configured to be gripped by a corresponding finger of the hand;
    the central portion is configured to be positioned between at least two fingers of the hand during grip of the handle by the hand;
    the sensing field is configured to cover a region including one or more fingers of the hand touching either of the two grip members;
    the one or more degrees of freedom include a roll degree of freedom;
    the handle is rotatable about the central axis of the handle with respect to the base member in the roll degree of freedom; and
    the sensing field is configured to include at least a portion of the hand at all orientations of the handle in the roll degree of freedom while the hand grips the handle.

11. A control input device comprising:
    a handle configured to be manually contacted at a grip portion of the handle and moved by a hand of a user in one or more degrees of freedom, wherein the handle includes a central portion that extends along a central axis of the handle, and wherein the central portion is configured to be positioned between at least two fingers of the hand during a grip of the handle by the hand;

one or more control input sensors configured to detect positions or orientations of the handle in the one or more degrees of freedom; and a presence sensing system including a presence sensor coupled to a distal end of the handle that is proximate to the hand, wherein the presence sensor is configured to detect electromagnetic radiation or an ultrasonic wave that is directed through space to the presence sensor by a presence of the hand in a sensing field of the presence sensor, and wherein the sensing field is located proximate to the handle, wherein a signal generated by the presence sensing system comprises a parameter, the parameter comprising a value that indicates:
- a direction of motion of the hand in the sensing field relative to the presence sensor, or
- a velocity of the hand in the sensing field, wherein the velocity includes the direction of motion of the hand in the sensing field relative to the presence sensor.

12. The control input device of claim 11, wherein:
the parameter additionally indicates a variable distance between the hand in the sensing field and the presence sensor.

13. The control input device of claim 11, wherein:
the presence sensor includes at least one of an electromagnetic sensor, a thermopile sensor, or a thermal imaging camera;
the electromagnetic sensor includes an emitter and a detector, the emitter being configured to emit a first electromagnetic signal in the sensing field, and the detector being configured to detect the first electromagnetic signal reflected from the hand in the sensing field;
the thermopile sensor includes a detector configured to detect infrared radiation emitted by the hand in the sensing field; and
the thermal imaging camera includes a detector configured to detect the infrared radiation emitted by the hand in the sensing field.

14. A method comprising:
activating a non-controlling mode in which a handle of a control input device is manually moveable by a user in one or more degrees of freedom without moveably controlling a manipulator device in communication with the control input device;
in the non-controlling mode, sensing a presence of a hand of a user relative to the handle in a sensing field of a presence sensor, a portion of the sensing field being located proximate to the handle, wherein sensing the presence of the hand of the user includes:
- determining a direction of motion of the hand relative to the handle, or
- determining a velocity of the hand relative to the handle, wherein the velocity includes the direction of motion of the hand relative to the handle; and in response to sensing the presence of the hand, activating a controlling mode of the control input device in which the handle is moveable by the user in the one or more degrees of freedom to moveably control the manipulator device.

15. The method of claim 14, wherein:
sensing the presence of the hand includes determining the velocity of the hand relative to the handle;

the method further comprises:
determining that the velocity of the hand meets a threshold velocity and that the direction of motion of the hand is in a particular direction relative to the handle; and
the activation of the controlling mode is performed in response to the velocity of the hand meeting the threshold velocity and the direction of motion of the hand is in the particular direction relative to the handle.

16. The method of claim 14, wherein:
the method further comprises activating the non-controlling mode in response to sensing an indication that the hand is no longer operating the handle; and
the indication includes at least one of sensing the hand outside a threshold distance from the handle or sensing the hand moving in a particular direction relative to the handle.

17. The method of claim 14, wherein:
the method further comprises while in the controlling mode:
determining a position of the hand in the sensing field of the presence sensor relative to a reference location of the control input device while in the controlling mode, and
determining, based on the position of the hand, one or more characteristics of force to be output on the control input device; and
the one or more characteristics of force include at least one of: a maximum force magnitude output on the control input device, a gain of force magnitude output on the control input device, or a rate at which a magnitude of the force on the control input device is increased.

18. The method of claim 14, wherein:
the method further comprises while in the controlling mode:
determining a position of the hand in the sensing field of the presence sensor relative to a reference location of the control input device; and
adjusting a safety feature of the control input device based on the position; and adjusting the safety feature includes at least one of:
changing parameters used in detection of patterns of motion, acceleration, or direction of the control input device to detect active use of the control input device by the user, or
physically limiting a velocity of the control input device in one or more degrees of freedom by using one or more force output devices coupled to a mechanism of the control input device.

19. The method of claim 14, wherein:
the method further comprises:
detecting presence of the user by one or more other presence sensors of the control input device; and
determining one or more detection parameters of a hand presence sensing system based on the detected presence of the user by the one or more other presence sensors;
the other presence sensors are independent and separate from the hand presence sensing system that performs the sensing of the presence of the hand; and
the one or more detection parameters of the hand presence sensing system include one or more of: a velocity threshold of sensing, a direction threshold of sensing, a range of sensing, or a duration of sensing.

20. The control input device of claim 1, wherein the presence sensor is configured to provide the value to a processor configured to determine whether the hand is operating the handle based on the value and based on whether the direction of motion is toward or away from the handle.

* * * * *